(12) United States Patent
Shimer et al.

(10) Patent No.: US 11,484,664 B2
(45) Date of Patent: Nov. 1, 2022

(54) HUBER SAFETY NEEDLE

(71) Applicant: Medical Components, Inc., Harleysville, PA (US)

(72) Inventors: Kurt Shimer, Greensboro, NC (US); Matthew Gunn, North Wales, PA (US); Raymond Bizup, Feasterville, PA (US)

(73) Assignee: Medical Components, Inc., Harleysville, PA (US)

( * ) Notice: Subject to any disclaimer, the term of this patent is extended or adjusted under 35 U.S.C. 154(b) by 114 days.

(21) Appl. No.: 16/577,234

(22) Filed: Sep. 20, 2019

(65) Prior Publication Data

US 2020/0009327 A1    Jan. 9, 2020

Related U.S. Application Data

(63) Continuation of application No. 15/461,578, filed on Mar. 17, 2017, now Pat. No. 10,441,727.
(Continued)

(51) Int. Cl.
*A61M 5/32*     (2006.01)
*A61M 5/158*    (2006.01)
(Continued)

(52) U.S. Cl.
CPC .......... *A61M 5/3232* (2013.01); *A61M 5/158* (2013.01); *A61M 5/3137* (2013.01); *A61M 5/3221* (2013.01); *A61M 5/3243* (2013.01); *A61M 5/3275* (2013.01); *A61M 5/34* (2013.01); *A61M 25/0612* (2013.01);
(Continued)

(58) Field of Classification Search
CPC ............ A61M 5/3232; A61M 25/0612; A61M 25/0625; A61M 5/3243; A61M 5/158; A61M 5/3275; A61M 5/3137; A61M 5/3221; A61M 5/34; A61M 2005/3247;
(Continued)

(56) References Cited

U.S. PATENT DOCUMENTS 4,627,843 A    12/1986  Raines
4,735,618 A     4/1988  Hagen
(Continued)

FOREIGN PATENT DOCUMENTS

CN          1878584 A    12/2006
CN        101415453 A     4/2009
(Continued)

*Primary Examiner* — Bhisma Mehta
*Assistant Examiner* — Hamza A Darb

(57) ABSTRACT

Disclosed is a Huber needle assembly that may include an upper body connected to a lower body, the assembly being structured to retain a needle for insertion/extraction of the needle into/from an insertion site. The upper body can statically retain the needle while the lower body may slidably receive the needle. The lower body can further include a catch that engages a tip of the needle and/or misaligns the tip of the needle with a needle aperture of the lower body to place the assembly in a safety-lock position, preventing rebound, needle-stick injury, and/or any type of exposure of the needle tip to an environment outside of the lower body. The assembly can further bias the needle in a direction so as to prevent re-emergence of the needle tip after being withdrawn into the lower body.

12 Claims, 21 Drawing Sheets

Related U.S. Application Data

(60) Provisional application No. 62/407,137, filed on Oct. 12, 2016, provisional application No. 62/310,130, filed on Mar. 18, 2016.

(51) Int. Cl.
*A61M 5/31* (2006.01)
*A61M 5/34* (2006.01)
*A61M 25/06* (2006.01)

(52) U.S. Cl.
CPC . *A61M 25/0625* (2013.01); *A61M 2005/1581* (2013.01); *A61M 2005/3247* (2013.01); *A61M 2005/342* (2013.01); *A61M 2205/581* (2013.01)

(58) Field of Classification Search
CPC .... A61M 2005/1581; A61M 2005/342; A61M 2205/581
See application file for complete search history.

(56) References Cited

U.S. PATENT DOCUMENTS

| | | |
|---|---|---|
| 4,737,144 A | 4/1988 | Choksi |
| 4,887,998 A | 12/1989 | Martin et al. |
| 4,978,344 A | 12/1990 | Dombrowski et al. |
| 5,037,401 A | 8/1991 | DeCamp |
| 5,059,180 A | 10/1991 | McLees |
| 5,171,303 A | 12/1992 | DeCamp |
| 5,300,046 A | 4/1994 | Scarfone et al. |
| 5,322,517 A | 6/1994 | Sircom et al. |
| 5,328,482 A | 7/1994 | Sircom et al. |
| 5,382,240 A | 1/1995 | Lam |
| 5,429,636 A | 7/1995 | Shikhman et al. |
| 5,507,730 A | 4/1996 | Haber et al. |
| 5,531,704 A | 7/1996 | Knotek |
| 5,611,781 A | 3/1997 | Sircom et al. |
| 5,662,610 A | 9/1997 | Sircom |
| 5,693,022 A | 12/1997 | Haynes |
| 5,697,907 A | 12/1997 | Gaba |
| 5,743,883 A | 4/1998 | Visconti |
| 5,823,997 A | 10/1998 | Thorne |
| 5,879,337 A | 3/1999 | Kuracina et al. |
| 5,925,020 A | 7/1999 | Nestell |
| 5,951,522 A | 9/1999 | Rosato et al. |
| 5,951,525 A | 9/1999 | Thorne et al. |
| 5,957,892 A | 9/1999 | Thorne |
| 5,997,504 A | 12/1999 | Bell |
| 6,001,080 A | 12/1999 | Kuracina et al. |
| 6,015,397 A | 1/2000 | Elson et al. |
| 6,117,108 A | 9/2000 | Woehr et al. |
| 6,161,630 A | 12/2000 | Stump et al. |
| 6,254,575 B1 | 7/2001 | Thorne, Jr. et al. |
| 6,261,259 B1 | 7/2001 | Bell |
| 6,280,420 B1 | 8/2001 | Ferguson et al. |
| 6,287,278 B1 | 9/2001 | Woehr et al. |
| 6,443,929 B1 | 9/2002 | Kuracina et al. |
| 6,488,667 B1 | 12/2002 | Murphy |
| 6,537,255 B1 | 3/2003 | Raines |
| 6,592,556 B1 | 7/2003 | Thorne |
| 6,595,955 B2 | 7/2003 | Ferguson et al. |
| 6,613,015 B2 | 9/2003 | Sandstrom et al. |
| 6,616,630 B1 | 9/2003 | Woehr et al. |
| 6,623,462 B2 | 9/2003 | Guzzo et al. |
| 6,629,959 B2 | 10/2003 | Kuracina et al. |
| 6,663,604 B1 | 12/2003 | Huet |
| 6,676,633 B2 | 1/2004 | Smith et al. |
| 6,719,721 B1 | 4/2004 | Okazaki et al. |
| 6,719,731 B2 | 4/2004 | Parmigiani |
| 6,752,791 B2 | 6/2004 | Murphy et al. |
| 6,796,962 B2 | 9/2004 | Ferguson et al. |
| 6,796,968 B2 | 9/2004 | Ferguson et al. |
| 6,824,530 B2 | 11/2004 | Wagner et al. |
| 6,860,871 B2 | 3/2005 | Kuracina et al. |
| 6,878,136 B2 | 4/2005 | Fleury et al. |
| 6,884,224 B2 | 4/2005 | Dalton |
| 6,902,546 B2 | 6/2005 | Ferguson |
| 6,918,894 B2 | 7/2005 | Fleury et al. |
| 6,926,693 B2 | 8/2005 | Enns |
| 6,932,803 B2 | 8/2005 | Newby |
| 6,939,331 B2 | 9/2005 | Ohshima |
| 6,949,086 B2 | 9/2005 | Ferguson et al. |
| 6,969,372 B1 | 11/2005 | Halseth |
| 6,984,213 B2 | 1/2006 | Horner et al. |
| 6,997,902 B2 | 2/2006 | Thorne et al. |
| 7,004,927 B2 | 2/2006 | Ferguson et al. |
| 7,008,402 B2 | 3/2006 | Ferguson et al. |
| 7,029,461 B2 | 4/2006 | Ferguson et al. |
| 7,097,637 B2 | 8/2006 | Triplett et al. |
| 7,125,397 B2 | 10/2006 | Woehr et al. |
| 7,125,398 B2 | 10/2006 | Garcia, Jr. |
| 7,144,389 B2 | 12/2006 | Ferguson et al. |
| 7,179,244 B2 | 2/2007 | Smith et al. |
| 7,198,618 B2 | 4/2007 | Ferguson et al. |
| 7,214,211 B2 | 5/2007 | Woehr et al. |
| 7,226,434 B2 | 6/2007 | Carlyon et al. |
| 7,264,613 B2 | 9/2007 | Woehr et al. |
| 7,291,135 B2 | 11/2007 | Ono |
| 7,341,573 B2 | 3/2008 | Ferguson et al. |
| 7,347,842 B2 | 3/2008 | Thorne et al. |
| 7,357,784 B2 | 4/2008 | Ferguson |
| 7,413,562 B2 | 8/2008 | Ferguson et al. |
| 7,422,573 B2 | 9/2008 | Wilkinson et al. |
| 7,438,703 B2 | 10/2008 | Barrus et al. |
| 7,455,664 B2 | 11/2008 | Fleury et al. |
| 7,458,954 B2 | 12/2008 | Ferguson et al. |
| 7,534,231 B2 | 5/2009 | Kuracina et al. |
| 7,549,979 B2 | 6/2009 | Enns et al. |
| 7,569,044 B2 | 8/2009 | Triplett et al. |
| 7,608,057 B2 | 10/2009 | Woehr et al. |
| 7,611,485 B2 | 11/2009 | Ferguson |
| 7,611,487 B2 | 11/2009 | Woehr et al. |
| 7,618,395 B2 | 11/2009 | Ferguson |
| 7,625,360 B2 | 12/2009 | Woehr et al. |
| 7,717,888 B2 | 5/2010 | Vaillancourt et al. |
| 7,758,544 B2 | 7/2010 | Solomon et al. |
| 7,762,992 B2 | 7/2010 | Triplett et al. |
| 7,776,016 B1 | 8/2010 | Halseth et al. |
| 7,858,774 B2 | 12/2010 | Ionescu et al. |
| 7,927,314 B2 | 4/2011 | Kuracina et al. |
| 3,002,746 A1 | 8/2011 | Erskine |
| 8,142,446 B2 | 3/2012 | Shan |
| 8,152,770 B2 | 4/2012 | Reid |
| D686,316 S | 7/2013 | Baid |
| 8,496,626 B2 | 7/2013 | Hiraoka et al. |
| D687,548 S | 8/2013 | Hayashi |
| 8,500,703 B2 | 8/2013 | Lambert |
| 8,574,197 B2 | 11/2013 | Halseth et al. |
| 8,834,422 B2 | 9/2014 | Walker et al. |
| D716,444 S | 10/2014 | Khalaj |
| D731,641 S | 6/2015 | Du |
| 9,248,234 B2 | 2/2016 | Barron |
| 2001/0039401 A1 | 11/2001 | Ferguson et al. |
| 2002/0099338 A1 | 7/2002 | Young |
| 2002/0173749 A1 | 11/2002 | Wagner et al. |
| 2003/0114797 A1 | 6/2003 | Vaillancourt et al. |
| 2003/0163097 A1 | 8/2003 | Fleury et al. |
| 2003/0163098 A1 | 8/2003 | Fleury et al. |
| 2004/0049159 A1 | 3/2004 | Barrus et al. |
| 2004/0082922 A1 | 4/2004 | Fleury et al. |
| 2004/0087912 A1 | 5/2004 | Swenson |
| 2004/0138613 A1 | 7/2004 | Reid |
| 2004/0147881 A1 | 7/2004 | Hyun |
| 2004/0167477 A1* | 8/2004 | Wilkinson ....... A61B 5/150656 604/263 |
| 2004/0220528 A1 | 11/2004 | Garcia, Jr. |
| 2005/0080386 A1 | 4/2005 | Reid |
| 2005/0107748 A1 | 5/2005 | Thorne et al. |
| 2006/0047252 A1 | 3/2006 | Ono |
| 2006/0064061 A1* | 3/2006 | Solomon ............... A61M 5/158 604/110 |
| 2006/0074387 A1 | 4/2006 | Thorne et al. |
| 2006/0129106 A1 | 6/2006 | Ferguson et al. |

(56) References Cited

U.S. PATENT DOCUMENTS

| | | |
|---|---|---|
| 2007/0010622 A1 | 1/2007 | Naito et al. |
| 2007/0106222 A1 | 5/2007 | Bennett |
| 2007/0282275 A1 | 12/2007 | Ferguson et al. |
| 2008/0097304 A1 | 4/2008 | Thorne |
| 2008/0119795 A1 | 5/2008 | Erskine |
| 2008/0171986 A1 | 7/2008 | Baid |
| 2008/0208139 A1 | 8/2008 | Scheurer et al. |
| 2008/0262434 A1 | 10/2008 | Vaillancourt |
| 2009/0062744 A1 | 3/2009 | Weilbacher et al. |
| 2009/0137958 A1 | 5/2009 | Erskine |
| 2009/0163875 A1 | 6/2009 | Hiraoka et al. |
| 2009/0249605 A1 | 10/2009 | Erskine |
| 2009/0299302 A1 | 12/2009 | Lambert |
| 2010/0082002 A1 | 4/2010 | Baid |
| 2010/0137815 A1 | 6/2010 | Kuracina et al. |
| 2010/0280413 A1 | 11/2010 | Ferguson et al. |
| 2011/0166526 A1 | 7/2011 | Kuracina et al. |
| 2011/0220274 A1 | 9/2011 | Erskine |
| 2011/0276013 A1 | 11/2011 | Saitoh et al. |
| 2012/0012332 A1 | 1/2012 | Rooks |
| 2012/0123332 A1 | 5/2012 | Erskine |
| 2014/0296795 A1 | 10/2014 | Adams et al. |
| 2016/0058954 A1* | 3/2016 | Gunn .................. A61M 5/158 604/263 |
| 2016/0074596 A1* | 3/2016 | Mantsch .............. A61M 5/158 604/263 |

FOREIGN PATENT DOCUMENTS

| | | |
|---|---|---|
| EP | 1116493 A1 | 7/2001 |
| EP | 1186313 A1 | 3/2002 |
| EP | 1430921 A2 | 6/2004 |
| EP | 2016964 A1 | 1/2009 |
| EP | 2609953 A1 | 7/2013 |
| EP | 2827924 A1 | 1/2015 |
| GB | 1233302 A | 5/1971 |
| JP | 2001-224682 A | 8/2001 |
| JP | 2001515767 A | 9/2001 |
| JP | 2003044975 A | 2/2003 |
| JP | 2003076520 A | 3/2003 |
| JP | 2003195227 A | 7/2003 |
| JP | 2003275310 A | 9/2003 |
| JP | 2003299735 A | 10/2003 |
| JP | 2004195227 A | 7/2004 |
| JP | 2006-61379 A | 3/2006 |
| JP | 2007-511285 A | 5/2007 |
| JP | 2008013112 A | 1/2008 |
| JP | 2008212645 A | 9/2008 |
| JP | 2009142658 A | 7/2009 |
| JP | 2010207634 A | 9/2010 |
| JP | 2011053640 A | 3/2011 |
| JP | 2011115615 A | 6/2011 |
| JP | 2012-016629 A | 1/2012 |
| JP | 2013138853 A | 7/2013 |
| JP | 2015134156 A | 7/2015 |
| WO | 99/07424 A1 | 2/1999 |
| WO | 02/087672 A1 | 11/2002 |
| WO | 2005/049109 A2 | 6/2005 |
| WO | 2005/120624 A1 | 12/2005 |
| WO | 2006/085176 A1 | 8/2006 |
| WO | 2006/096633 A1 | 9/2006 |
| WO | 2006/096634 A1 | 9/2006 |
| WO | 2006/096635 A1 | 9/2006 |
| WO | 2006/096636 A1 | 9/2006 |
| WO | 2010/101573 A1 | 9/2010 |
| WO | 2013/139476 A1 | 9/2013 |

* cited by examiner

HUBER SAFETY NEEDLE

CROSS-REFERENCES TO RELATED APPLICATIONS

This application is a continuation application of U.S. application Ser. No. 15/461,578, filed Mar. 17, 2017, which claims the benefit of priority to U.S. Provisional application No. 62/310,130, filed Mar. 18, 2016, and U.S. Provisional application No. 62/407,137, filed Oct. 12, 2016, the entire contents of which are incorporated herein by reference.

BACKGROUND OF THE INVENTION

Field of the Invention

The subject matter disclosed herein generally relates to a Huber needle assembly. More specifically, the subject matter herein relates to a Huber needle assembly with a means to generate a safety-lock position by biasing the needle away from the needle aperture to prevent re-emergence of the needle tip from the assembly.

Background of the Related Art

Known Huber needle assemblies are generally widely used in hospitals and alternate care sites, where these Huber needle assemblies are generally used in conjunction with implanted ports. Such Huber needle assemblies can provide a non-coring needle that may be used to administer chemotherapy, intravenous ("IV") fluids, medications, total parenteral nutrition, or to transfuse blood products through implanted ports. The implanted port generally contains a self-sealing septum that seals around the needle, holds the needle in place, and allows for multiple accessing by a Huber needle through an insertion site.

The known Huber needle assembly may be designed for safety of the patient; however, it presents a considerable risk to the user of such a Huber needle assembly. For example, use of a known Huber needle assembly can expose the user to blood borne pathogens, drugs, and/or medication being administered through the Huber needle, regardless of whether the known Huber needle assembly is used properly or improperly. Some reasons for this may include a failure in the art to provide a Huber needle assembly that effectively prevents rebound of the needle, prevents inadvertent needle stick injury to a user of the assembly, and/or prevents exposure of the needle tip when the assembly is placed into a "safety" position.

For example, known Huber needle assemblies may require two hands to extract the needle from the implanted port. With such systems, a first hand is typically used to stabilize the implanted port and/or Huber needle assembly while a second hand is used to withdraw the needle. Removal of the needle while the first hand is in the area of the insertion site can present a significant risk of inadvertent needle-stick injury to the first hand. Further, the force required to withdraw the needle from a self-sealing septum of the implanted port can cause a user to over-extend the structure of the known Huber needle assembly, whereby the resilient nature of the material comprising the structure causes the needle to rebound, resulting in further risk of a needle-stick injury to the user. Such a needle-stick injury can result in transfer of blood borne pathogens, such as Hepatitis, Human Immunedeficiency Virus ("HIV"), etc. In addition to blood borne pathogens, healthcare workers that prepare hazardous drugs, mix drugs, and/or administer drugs can be at risk for exposure to the drug if such a needle-stick injury occurs. Even when drugs are carefully handled, exposure can result from inhalation or direct skin contact with the drug due to exposure to the needle tip.

The present invention is directed toward overcoming one or more of the above-identified problems.

BRIEF SUMMARY OF THE INVENTION

The Huber needle assembly can include an upper body connected to a lower body, where the assembly may be structured to retain a needle for insertion/extraction of the needle into/from an insertion site. The upper body can be structured to statically retain the needle while the lower body can be structured to slidably receive the needle so that the upper body and needle can move in unison, but both move relative to the lower body. The lower body can further include a catch that engages the needle tip to place the assembly in a safety-lock position, preventing rebound, needle-stick injury, and/or any type of exposure of the needle tip to an environment outside of the lower body.

In at least one embodiment, as the upper body is moved away from the lower body the needle can be caused to move along with the upper body, facilitating extraction of the needle from the insertion site. The upper body can be caused to further move away from the lower body until a tip of the needle engages a catch of the lower body, placing the assembly in a safety-lock position. In a further embodiment, the assembly can be placed into the safety-lock position by biasing the needle away from the needle aperture of the lower body, thereby preventing re-emergence of the needle tip. In the safety-lock position, the assembly can envelope the needle tip within an enveloping structure, prevent any further movement of the needle tip beyond the enveloping structure, and/or sheath the needle tip so as to prevent any type of exposure of the needle tip.

In an exemplary embodiment, a Huber needle assembly can include an upper body mechanically and operatively connected with a lower body so as to provide support for a needle and facilitate movement of the upper body along an operational longitudinal direction of the assembly to cause the needle to move relative to the lower body; wherein the lower body has a lower body needle aperture formed within a portion thereof and a catch formed adjacent the lower body needle aperture; wherein the needle comprises a needle shaft leading to a needle tip, wherein both of the needle shaft and the needle tip are slidably received by the lower body needle aperture; and, wherein movement of the upper body away from the lower body retracts the needle tip within the lower body through the lower body needle aperture and urges the needle in an operational latitudinal direction, and when the needle tip enters a portion of the catch, the needle tip at least one of becomes misaligned with the lower body needle aperture and engages the catch. The upper body and the lower body may be connected by a connector, the connector limiting a distance at which the upper body is separated from the lower body so that the needle tip does not extend beyond a top of the lower body. The catch can include a well having a bottom surface and at least a portion of the bottom surface is sloped. The needle may be further biased in the operational latitudinal direction via at least one of an advancing assist and a spring, each configured to impose a force on the needle to urge the needle in the operational latitudinal direction. At least one of the upper body and lower body can be capable of tilting. The tilting may facilitate at least one of the misalignment of the needle tip with the lower body aperture and the engagement of the needle tip with the catch.

When at least one of the misalignment of the needle tip with the lower body needle aperture and the engagement of the needle tip with the catch occurs, an audible sound may emanate from the assembly. The advancing assist can be disposed on a portion of the connector, and movement of the upper body away from the lower body may force the advancing assist to make contact with the needle shaft and further urges the needle in the operational latitudinal direction.

In another exemplary embodiment a Huber needle assembly can include an upper body having an upper body needle aperture formed therein; a lower body having a lower body needle aperture and a well, wherein the lower body needle aperture leads into at least a portion of the well, wherein a volume of space extending from the well bottom surface to a top of the lower body is an enveloping structure; and, a connector connecting the upper body to the lower body, the connector facilitating movement of the upper body along an operational longitudinal direction and limiting a separation distance between the upper body and the lower body to prevent the needle tip from extending beyond the top of the lower body; wherein movement of the upper body away from the lower body retracts the needle tip within the lower body through the lower body needle aperture and biases the needle away from the lower body needle aperture. Biasing the needle may further comprise causing the needle tip to at least one of become misaligned with the lower body needle aperture and engage a portion of the well. The needle can be further biased in the operational latitudinal direction via at least one of an advancing assist and a spring, each configured to impose a force on the needle to urge the needle in the operational latitudinal direction. In some embodiments, the connector is connected to the upper body by an upper body connection, the connector is connected to the lower body by a lower body connection, and at least one of a geometric plane of the upper body connection and a geometric plane of the lower body connection is offset from an axis of an operational longitudinal direction. The biasing can be at least one of urging the needle in a forward operational latitudinal direction when the upper body is moved away from the lower body and preventing the needle tip from moving in a rearward operational latitudinal direction after the needle tip has entered the enveloping structure. The enveloping structure may be configured to envelope the needle tip after the needle tip has entered the enveloping structure, preventing exposure of the needle tip to an environment outside of the enveloping structure. The enveloping structure may further include a flange extension disposed on the top of the lower body. In some embodiments, the biasing of the needle further includes generating an audible sound. Further, at least one of the upper body and lower body may be capable of tilting. The tilting may facilitate the biasing of the needle.

In another exemplary embodiment, a Huber needle assembly can include an upper body having an upper body needle aperture formed therein; a lower body having a lower body needle aperture and a well, wherein the lower body needle aperture leads into at least a portion of the well; a connector connecting the upper body to the lower body, the connector facilitating movement of the upper body along an operational longitudinal direction and limiting a separation distance between the upper body and the lower body to prevent the needle tip from extending beyond the top of the lower body; and, a biasing means to bias the needle away from the lower body needle aperture. Movement of the upper body away from the lower body can retract the needle tip within the lower body through the lower body needle aperture, where the biasing means urges the needle away from the lower body needle aperture. The biasing means can include at least one of: an advancing assist configured to impose a force on the needle to urge the needle in an operational latitudinal direction; a spring configured to impose a force on the needle to urge the needle in the operational latitudinal direction; and, a tilting motion of at least one of the upper body and lower body. In some embodiment, the biasing of the needle further includes generating an audible sound. In some embodiments, the lower body may tilt to cause the needle tip to at least one of misalign with the lower body aperture and the engage the catch.

While these potential advantages are made possible by technical solutions offered herein, they are not required to be achieved. The presently disclosed invention can be implemented to achieve technical advantages, whether or not these potential advantages, individually or in combination, are sought or achieved.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present invention will be more apparent from the following more particular description thereof, presented in conjunction with the following drawings, in which:

FIG. 7A-7C show the assembly in a fully closed position, FIGS. 7D-7F show the assembly in an intermediary position between a fully closed position and a fully open position, and FIG. 7G shows the assembly in a fully open position.

DETAILED DESCRIPTION OF THE INVENTION

Figure 1:
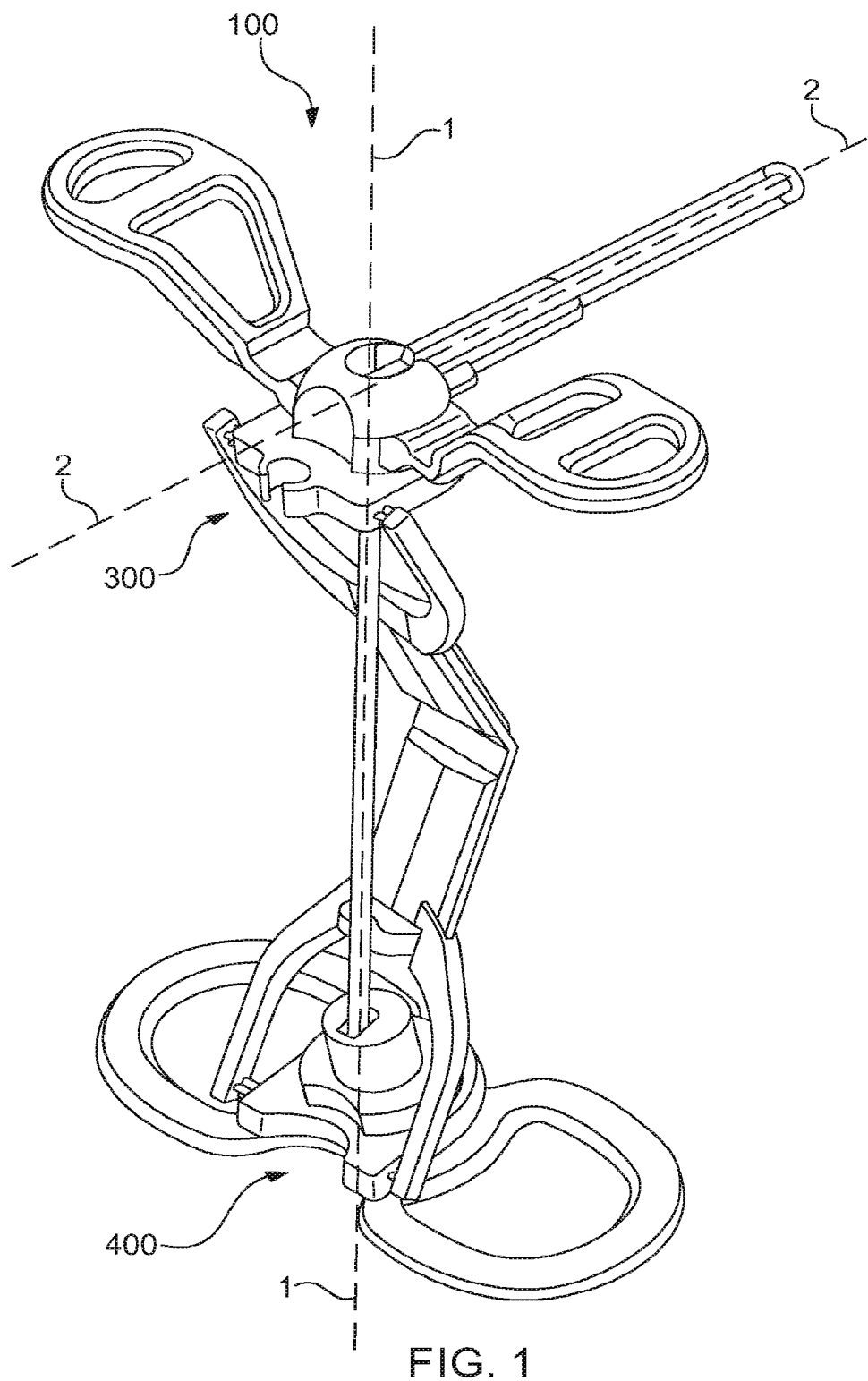
FIG. 1 is a perspective view of an exemplary Huber needle assembly.
Figure 2:
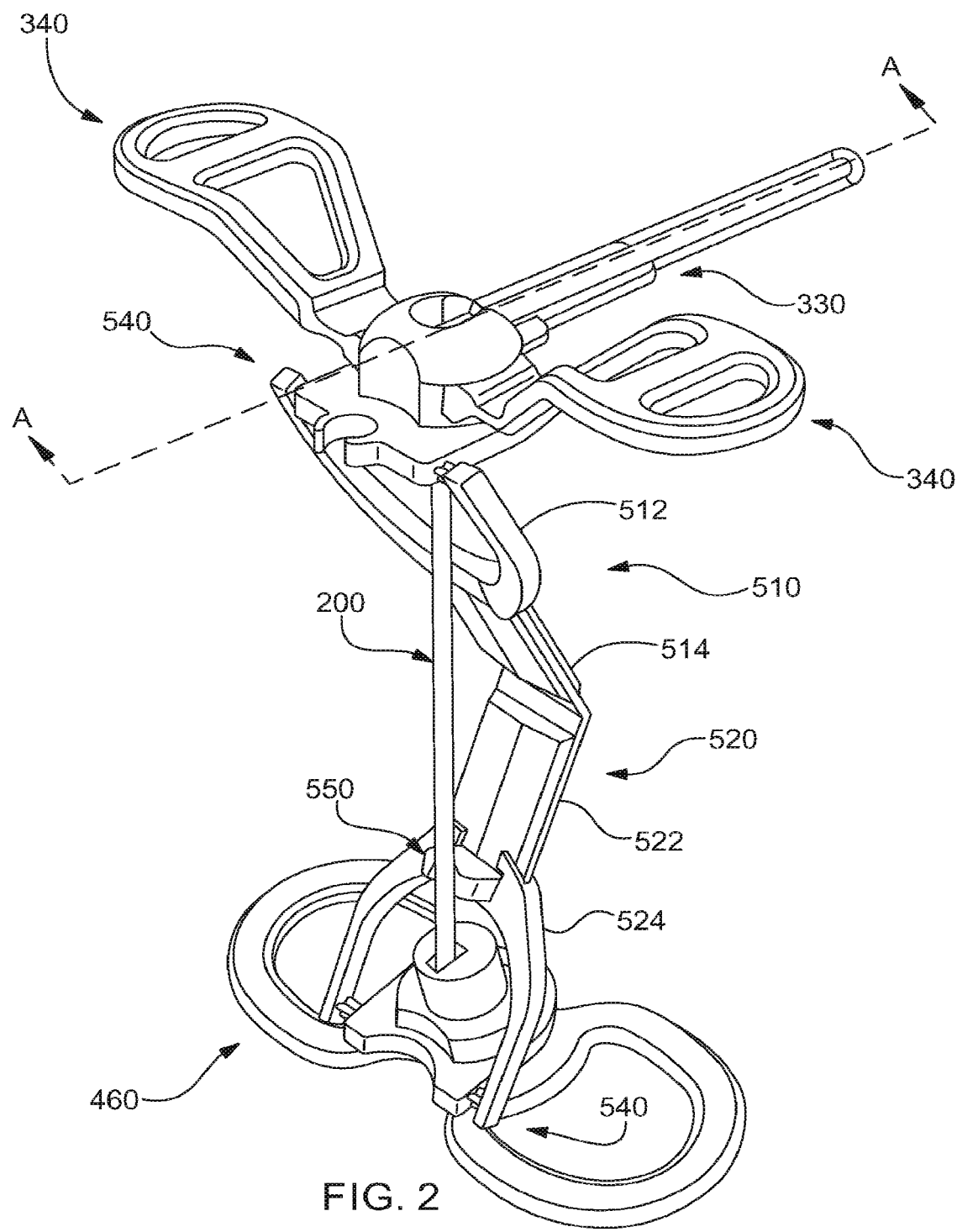
FIG. 2 is another perspective view of the Huber needle assembly.

The following description is of an embodiment presently contemplated for carrying out the present invention. This description is not to be taken in a limiting sense, but is made merely for the purpose of describing the general principles and features of the present invention. The scope of the present invention should be determined with reference to the claims.

The Huber needle assembly 100 is an apparatus that may be structured to provide support for a needle 200 and facilitate insertion/extraction of the needle 200 into/therefrom a body of a being. In some embodiments, the assembly 100 can be structured to support a Huber style needle 200. In further embodiments, the assembly 100 can be structured to facilitate insertion/extraction of a needle 200 into/therefrom an implantable port (not shown) that may have been implanted into the body of the being.

The assembly 100 can include an upper body 300 and a lower body 400, and may be configured such that the upper body 300 is situated above the lower body 400 so that the upper body 300 can move linearly along an operational longitudinal direction 1 of the assembly 100. The upper body 300 can be further structured to statically retain the needle 200 so that as the upper body 300 is moved, the needle 200 moves along with the upper body 300. The lower body 400 can be further structured to slidably secure the needle 200 but to allow independent movement of the needle 200 relative to the lower body 400. For example, the lower body 400 may allow the needle 200 to move along the operational longitudinal direction 1, but restrain, or at least partially restrain, movement of the needle 200 in a direction that is transverse to the operational longitudinal direction 1.

In use, the upper body 300 can be extended away from the lower body 400, and then the lower body 400 may be placed above and/or onto the body of a being and/or implantable port (i.e., the insertion site). The upper body 300 can then be forced to move toward the lower body 400 to cause the needle 200 to insert into the insertion site. Alternatively, and preferably in some embodiments, the assembly 100 can already be arranged to have the upper body 300 advanced toward the lower body 400 so that a practitioner can insert the needle 200 into the insertion site by positioning the assembly 100 over the insertion site and forcing all three components of the upper body 300, the lower body 400, and the needle 200 simultaneously and in unison toward the insertion site, thereby causing the needle 200 to insert into the insertion site. Once the needle 200 has been inserted into the insertion site, medical treatment can ensue. After treatment, the upper body 300 may then be moved away from the lower body while the lower body 400 is caused to remain stationary. This can include causing the lower body 400 to remain in a stationary position above and/or on the insertion site. As the upper body 300 is moved away from the lower body 400, the needle 200 can be caused to move along with the upper body 300 so that both the upper body 300 and needle 200 move simultaneously but also move independently of, and relative to, the lower body 400, thereby facilitating extraction of the needle 200 from the insertion site. The upper body 300 can be caused to further move away from the lower body 400 until a tip 250 of the needle 200 becomes misaligned with a lower body needle aperture 420 and/or engages a catch 430 of the lower body 400. The misalignment of the needle tip 250 with the lower body needle aperture 420 and/or the engagement of the needle tip 250 with the catch 430 can placed the assembly 100 in a safety-lock position. In some embodiments, the misalignment of the needle tip 250 with the lower body needle aperture 420 can be achieved by biasing the needle 200 away from the lower body needle aperture 420, thereby preventing re-emergence of the needle tip 250 from an interior of the lower body 400. In the safety-lock position, the assembly 100 can envelope the needle tip 250 within an enveloping structure 450, prevent any further movement of the needle tip 250 beyond the enveloping structure 450, and/or sheath the needle tip 250 so as to prevent any type of exposure of the needle tip 250. The safety-lock position can prevent rebound, needle-stick injury, and/or any type of exposure of the needle tip 250 to an environment outside of the lower body 400.

Turning now to the figures, several specific embodiments are described in more detail. The various embodiments and features described in the depicted embodiments may be used either individually or in any appropriate combination, as the disclosure is not limited to any specific embodiment descripted herein.

Referring to FIGS. 1-5, any one or both of the upper body 300 and lower body 400 can be constructed from a lightweight rigid or semi-rigid material, such as plastic, polymer, lightweight metal, etc. Further, the assembly 100 may be structured so that the upper body 300 is connected to the lower body 400 by a connector 500. The connector 500 can be a pivot mechanism, hinge mechanism, tether, etc. that operatively connects the upper body 300 to the lower body 400. Further, the connector 500 can be structured to limit motion of the upper body 300 relative to the lower body 400. For example, the connector 500 can be a pivot mechanism that allows the upper body 300 to move relative to the lower body 400 in the operational longitudinal direction 1 and limits the distance at which the upper body 300 can be separated from the lower body 400.

In some embodiments, the connector 500 can be a first connector portion 510 attached to the upper body 300 and a second connector portion 520 attached to the lower body 400, where a mating point 530 of the first connector portion 510 with the second connector portion 520 forms a living hinge. The mating point 530 can also be a pivot hinge, barrel hinge, or other pivoting mechanism.

The connector 500 can include more or less connector portions. For example, the connector 500 can have first, second, and third connector portions, where the first connector portion is connected to the upper body 300, the first connector portion also being connected to the second connector portion via a mating point. The third connector portion can be connected to the lower body 400, the third connector portion also being connected to the second connector portion via a mating point.

As another example, the connector 500 can be a unitary flexible member that can bend and flex (e.g., a rubber member). As the upper body 300 and lower body 400 are moved towards each other, the unitary flexible member can bend out of the path of the upper body-lower body movement to form a contracted or folded position, and as the upper body 300 and lower body 400 move away from each other, the flexible member can be caused to straighten and/or even flex to form an extended or unfolded position.

Figure 4:
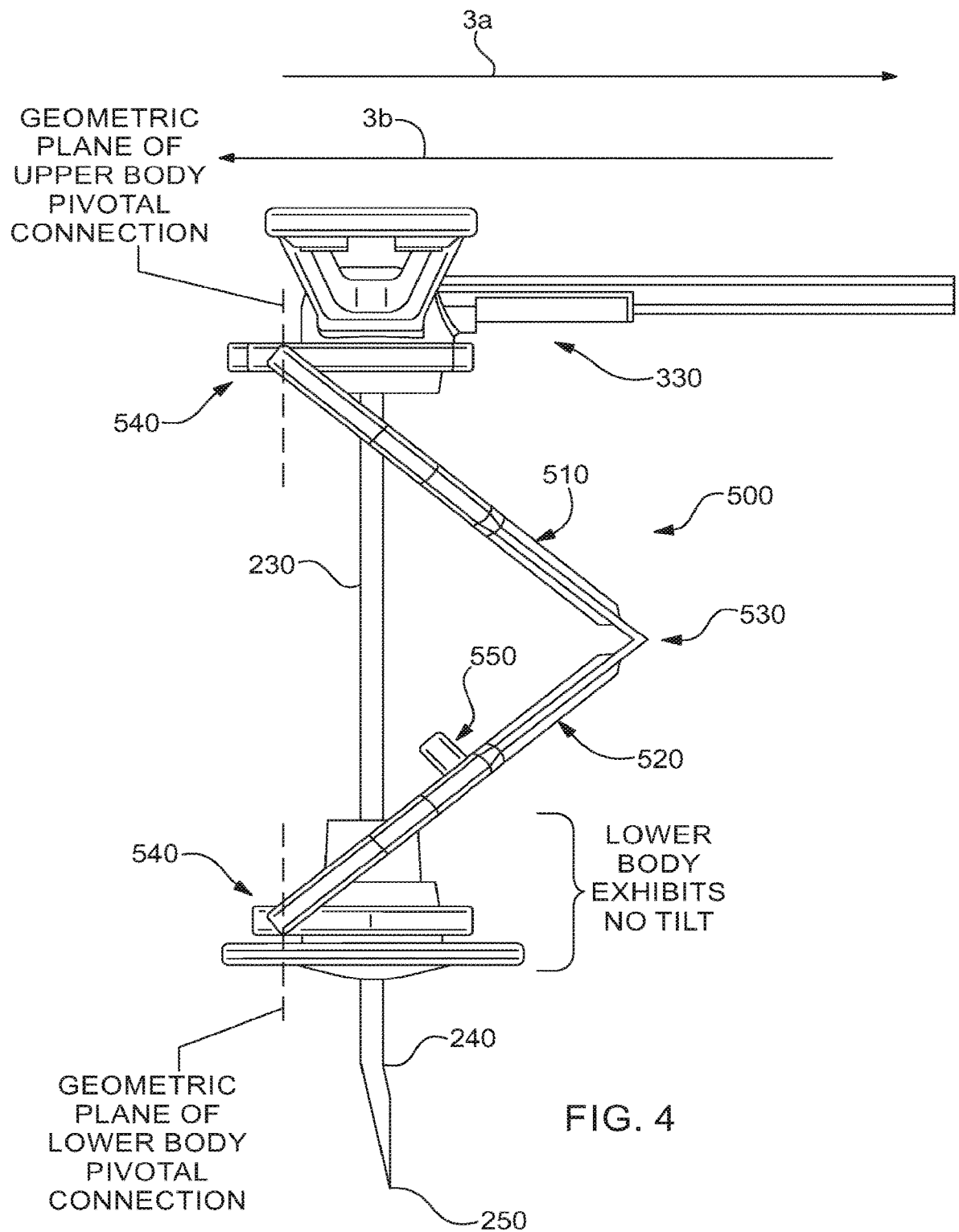
FIG. 4 is a side view of the Huber needle assembly in a non safety-lock position.

Further, the connector 500 can be structured such that the connector portion(s) bend and/or pivot in a predetermined direction. For example, the connector 500 can include the first connector portion 510 connected to the second connector portion 520 via the mating point 530 so that when the upper body 300 and lower body 400 move towards each other, the mating point 530 moves radially outward from an axis of the operational longitudinal direction 1. In some embodiments, the mating point 530 can be forced to move radially from the axis of the operational longitudinal direction 1 by moving in an operational latitudinal direction 2. As a non-limiting example, FIG. 4 shows the mating point 530 moving in a rearward operational latitude direction 3a when the upper body 300 and lower body 400 move towards each other and moved in a forward operational latitude direction 3b when the upper body 300 and lower body 400 move away from each other. This may be done to cause the connector 500 to be out of an area of operation and/or to prevent the connector 500 from obstructing a practitioner's view of the insertion site. Causing the connector 500 to pivot and/or bend in a predetermined direction can be achieve by forming a living hinge at the mating point 530 comprising a composite material where one side is more rigid than the other side so as to have a tendency to flex in a desired direction. Other ways to cause the connector 500 to pivot and/or bend in a predetermined direction can be used, which may include mechanical stops placed on any of the pivots of the assembly 100 for example.

As indicated above, the connector 500 can be structured to enable movement of the upper body 300 relative to the lower body 400 in the operational longitudinal direction 1. In some embodiments, the connector 500 can facilitate a range of motion from a fully closed position (e.g., a portion of the upper body 300 abutting a portion of the lower body 400) to a safety-lock position (e.g., the upper body 300 being moved away from the lower body 400 so that the needle tip 250 is positioned with the enveloping structure 450). The safety-lock position may also be referred to as the fully open position. Alternatively, the connector 500 can facilitate a range of motion that is between the fully closed position and the fully open position. For example, the connector 500 and/or any pivot of the connector 500 may include a mechanical stop that facilitates a range of motion that is an intermediary range between the fully closed position and the fully open position.

Referring to FIGS. 8A-8D, in an exemplary embodiment, the connector 500 can include the first connector portion 510 having its first connector portion top 512 pivotally attached to a portion of the upper body 300 via pivotal connection 540, and the second connector portion 520 having its second connector portion bottom 524 pivotally connected a portion of the lower body 400 via a pivotal connection 540. The pivotal connections 540 can be pivot and hub assemblies, torsion hinge assemblies, or any pivoting mechanism described herein. The first connector portion bottom 514 may be connected to the second connector portion top 522 via the mating point 530, which may be a living hinge. The connector 500 can be structured so that the mating point 530 moves in an operational latitudinal direction 2 during operation of the assembly. For example, the mating point 530 can move in the rearward operational latitude direction 3a when the upper body 300 is moved towards the lower body 400, and the mating point 530 can move in the forward operational latitude direction 3b when the upper portion 3 is moved away from the lower body 400.

The first connector portion 510 can have a general "Y" shape, where the first connector portion bottom 514 is the single prong of the "Y" and the first connector portion top 512 is the two-prong extension of the "Y". Each prong of the first connector portion top 512 can be made to straddle the upper body 300 and pivotally connect to the upper body 300 at the pivotal connection 540. The second connector portion 520 can have a general "Y" shape, where the second connector portion top 522 is the single prong of "Y" and the second connector portion bottom 524 is the two-prong extension of the "Y". Each prong of the second connector portion bottom 524 can be made to straddle the lower body 400 and pivotally connect to the lower body 400 at the pivotal connection 540.

Referring back to FIG. 4, a geometric plane of the upper body pivotal connection 540 and a geometric plane of the lower body pivotal connection 540 can be aligned to be within a same plane. Further, any one or both of the geometric planes of the upper body pivotal connection 540 and the lower body pivotal connection 540 can be parallel with an axis of the operational longitudinal direction 1. Any one or both of the geometric planes of the upper body pivotal connection 540 and the lower body pivotal connection 540 can be aligned with the axis of the operational longitudinal direction 1 so as to be coaxial with the axis of the operational longitudinal direction 1. Alternatively, any one or both of the geometric planes of the upper body pivotal connection 540 and the lower body pivotal connection 540 can be offset from the axis of the operational longitudinal direction 12. In other embodiments, the geometric plane of the upper body pivotal connection 540 and the geometric plane of the lower body pivotal connection 540 can be misaligned so as to not be in the same plane and/or not parallel with the axis of operational longitudinal direction 1. In an exemplary embodiment, the geometric planes of the upper body pivotal connection 540 and the lower body pivotal connection 540 are both parallel with the axis of the operational longitudinal direction 1, are both offset from the axis of the operational longitudinal direction 12 by being positioned more forward from the axis of the operational longitudinal direction 1, and are both in the same plane, as shown in FIG. 4.

In some embodiments, a portion of the connector 500 can include an advancing assist 550. As will be explained in detail later, the advancing assist 550 may be used to make contact with or engage the needle shaft 230 as the upper body 300 is moved away from the lower body 400, and urge the needle shaft 230 in the forward operational latitudinal direction 3b as the upper body 300 is further moved away from the lower body 400. As shown in FIGS. 8A-8D, the advancing assist 550 can be a protrusion extending from a side surface of the second connector portion 520. The advancing assist 550 can further include a channel 552 to guide the needle shaft into a detent or recess of the advancing assist 550. This may be done to ensure that the advancing assist 550 engages a shaft 230 of the needle 200 (e.g., the needle shaft 230 is received by the detent or recess of the channel 552) without the needle shaft 230 being deflected away from the advancing assist 550. In some embodiments, the urging of the needle shaft 230 in the forward operational latitudinal direction 3b can cause the needle tip 250 to become misaligned with the lower body needle aperture 420 and/or engage the catch 430, thereby preventing re-emergence of the needle tip 250 from an interior of the lower body 400. (See FIGS. 6B-6C). In other embodiments, the advancing assist 550 does not urge the needle shaft 230 in the forward operational latitudinal direction 3b, but rather prevents the needle tip 250 from moving in a rearward operational latitudinal direction 3a after the needle tip 250 has entered the enveloping structure 450 and thus ensures that the needle tip 250 does not disengage from the catch 430 and/or becomes aligned with the lower body needle aperture 420. For example, the offset of any one of the geometric planes of the upper body pivotal connection 540 and the lower body pivotal connection 540 with respect to the axis of the operational longitudinal direction 1 can cause the needle tip 250 to be urged in the forward operational latitude direction 3b as the upper body 300 is moved away from the lower body 400, thereby facilitating the misalignment of the needle tip 250 relative to the lower body needle aperture 420 and/or engagement of the needle tip 250 with the catch 430, wherein the advancing assist 550 may be used to prevent the needle tip 250 from moving in the rearward operational latitudinal direction 3a and becoming disengaged from the catch 430. As another example, and as will be explained in detail later, the catch 430 can include a well 432 with a sloped bottom surface 434, and the movement of the upper body 300 away from the lower body 400 can cause the needle tip 250 to enter the well 432 where the sloped bottom surface 434 causes the needle tip 250 to slide into a depression formed into the bottom surface 434 of the well 432. The sloped bottom surface 434 can trap the needle within the well 432. Again, the advancing assist 550 may be used to further prevent the needle tip 250 from moving in the rearward operational latitudinal direction 3a and becoming disengaged from the catch 430 and/or become aligned with the lower body needle aperture 420.

Any of the methods disclosed herein for urging the needle shaft 230 in a desired direction as the assembly 100 is transitioned from the closed position to the open position can be referred to as biasing the needle 200 and/or needle tip 250 away from the lower body needle aperture 420. Other means to bias the needle 200 and/or needle tip 250 will be discussed in detail later.

Referring to FIGS. 9A-9D, the upper body 300 can include an upper body hub 310, which may be a cylindrical member with a dome shaped top 312, a flat bottom 314, and an upper body needle aperture 320. The upper body needle aperture 320 can extend through the upper body hub 310 and further extend from an upper body hub top 312 to an upper body hub bottom 314. Extending from a portion of the upper body hub 310 can be a catheter retainer 330 configured to slidably receive a catheter and facilitate coupling the catheter with the needle 200. In some embodiments, the catheter retainer 330 is shaped as a semi-circular trough extending along the operational latitudinal direction 2, which may be in the rearward operational latitudinal direction 3a.

Figure 6A:
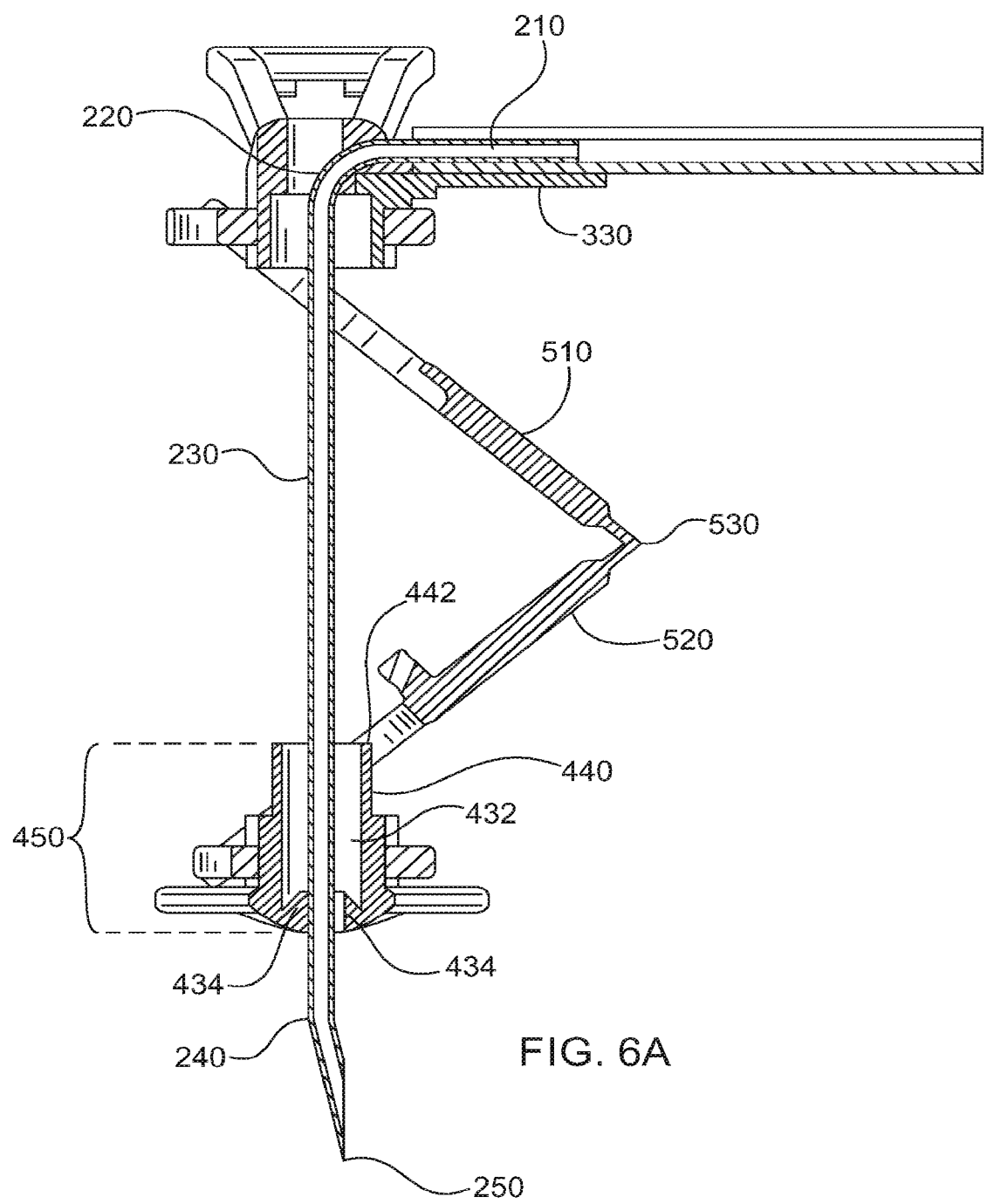
FIG. 6A is a side cross-sectional view taken alone the A-A line (see FIG. 2) of the Huber needle assembly with a well having a sloped bottom that extends all the way around the needle aperture.

As seen in FIG. 6A, it is envisioned for the needle 200 to include a bent or curved needle with a beveled section 240. For example, the needle 200 may include a connector end 210 leading to a bent section 220 forming an approximately ninety degree bend in the needle 200. Extending from the bent section 220 may be a straight needle shaft portion 230, which can lead to the beveled section 240 and then to the needle tip 250. The needle 200 can include a lumen formed within a central portion thereof and extending from the connector end 210 to the needle tip 250. The needle 200 can be disposed within the upper body hub 310 by allowing the needle tip 250 and needle shaft 230 to be slidebaly received by the upper body needle aperture 320 so that at least a portion of the bent section 220 and the connector end 210 resides within the catheter retainer 330. Thus, some embodiments include the upper body needle aperture 320 formed into a ninety degree bend to complement the ninety degree bend of the needle bent section 220 and facilitate reception of the needle 200. The extension of the upper body needle aperture 320 through the upper body hub bottom 314 can be made to be coaxial, or at least parallel, with the axis of the operational longitudinal direction 1. The extension the upper body needle aperture 320 through the upper body hub top 312 leading into the catheter retainer 330 can be made to be coaxial, or at least parallel, with an axis of the operational latitudinal direction 2. Once disposed within the upper body 300, the needle 200 can be permanently secured within the upper body 300, which may include statically securing the needle 200 within the upper body 300. For example, the upper body 300 can be formed by injection molding as a single piece with the needle 200 disposed within the upper body needle aperture 320 as described above. Alternatively, the upper body 300 can be formed from separate pieces and assembled together by adhesive and/or welding while the needle 200 is held in place within the upper needle aperture 320. In addition to these methods of fabrication, other suitable manufacturing means can be used.

Referring back to FIGS. 9A-9D, the upper body 300 may include at least one handle 340 extending from a surface of the upper body hub 310. In some embodiments, the upper body 300 includes two handles 20, each handle 340 extending from a diametrically opposing side of the upper body hub 310. In further embodiments, each handle 340 extends from a portion of the upper body hub 310 so as to be perpendicular to the operational latitudinal direction 2 and/or the operational longitudinal direction 1. Any handle 340 can be constructed of a rigid or a semi-rigid material, such as plastic, polymer, rubber, etc. In some embodiments, any one handle 340 can include a first handle member 342 and a second handle member 344, where the second handle member 344 extends at an angle relative to the first handle member 342. For example, the first handle member 342 can extend from a side surface of the upper body hub 310 at approximately forty-five degrees relative to the axis of the operational longitudinal direction 1, and the second handle member 344 can extend from the first handle member 342 at approximately ninety degrees relative to the axis of the operational longitudinal direction 1. Such an angled handle structure can improve ergonomics and facilitate easy manipulation of the assembly 100. In embodiments with at least two diametrically opposed handles 20, grasping the handles 20 can cause the handles 20 to rotate or bend so that top surfaces of the second handle member 344 of each handle abut each other. Again, this can improve ergonomics and facilitate easy manipulation of the assembly 100. Other handle 340 configurations and angles can be used. Further, any handle 340 can have an oval shape with an aperture formed therein.

Referring to FIGS. 10A-10F, the lower body 400 can include a lower body hub 410, which may be a cylindrical member with a lower body needle aperture 420. The lower body needle aperture 420 can extend through the lower body hub 410, which may include extending from a lower body hub top 412 to a lower body hub bottom 414. The lower body needle aperture 420 can be configured to slidably receive the needle tip 250 and needle shaft 230 so as to enable independent movement of the needle 200 and the upper body 300 relative to the lower body 400. For example, the lower body needle aperture 420 can have a diameter that is slightly larger than the diameter of the needle 200. Further, the diameter of the lower body needle aperture 420 can be large enough to accommodate slideable motion therethrough of the needle 200 and the beveled section 240. The lower body 400 can be formed by injection molding as a single piece, formed from separate pieces and assembled together by adhesive or welding, or by other suitable manufacturing means.

Disposed on the lower body hub bottom 414 can be a skin plate 470, where the lower body needle aperture 420 can be made to extend there-through. The skin plate 470 can be used to assist with stabilizing the assembly 100 onto the insertion site. For example, the skin plate 470 can have a contoured and/or textured surface to generate a nonslip interface between the skin plate 470 and the insertion site.

The lower body 400 may include at least one stabilization plate 460 extending from a surface of the lower body hub 410. In some embodiments, the lower body 400 includes two stabilization plates 460, each stabilization plate 460 extending from a diametrically opposing side of the lower body hub 410. In further embodiments, each stabilization plate 460 can extend from a portion of the lower body hub 410 so as to be perpendicular to the operational latitudinal direction 2 and/or the operational longitudinal direction 1. Any stabilization plate 460 can be constructed of a rigid or a semi-rigid material, such as plastic, polymer, rubber, etc. Further, any stabilization plate 460 can have an oval shape with an aperture formed therein.

Figure 6B:
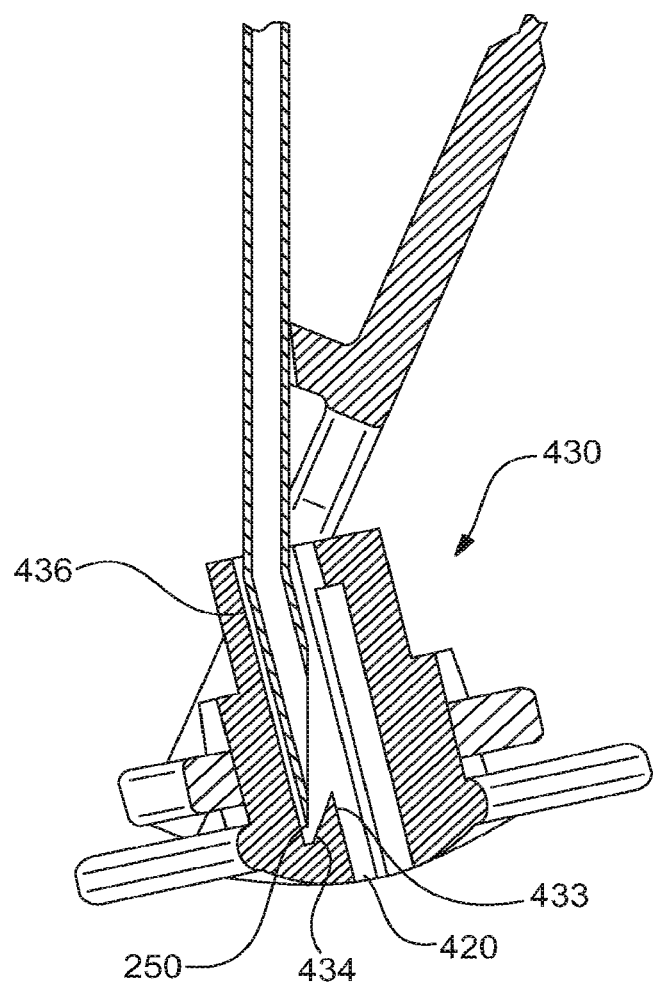
FIG. 6B is a close-up side cross-sectional view taken alone the A-A line of the Huber needle assembly with a well having a sloped bottom only at one side of the needle aperture.

Referring to FIGS. 6A-6B, two exemplary versions of the assembly 100 are disclosed. FIG. 6A shows a version with the well 432 having a sloped bottom surface 434 that extends all the way around the lower body needle aperture 420. FIG. 6B shows a version with the well 432 positioned to be adjacent the lower body needle aperture 420 and having a sloped bottom surface 434 only at one side of the lower body needle aperture 420. Generally, the extension of the lower body needle aperture 420 through the lower body hub 410 can be made to be coaxial, or at least parallel, with the axis of the operational longitudinal direction 1. As shown in the cross sectional views of FIGS. 6A-6B, the lower body needle aperture 420 can lead into the catch 430 formed into the lower body hub 410. For example, the catch 430 can be a bore made into an upper portion of the lower body hub 410, wherein the diameter of the bore can be greater than the lower body needle aperture 420. Thus, the catch 430 can be the well 432 defined by the bore with the lower body needle aperture 420 extending through the bottom surface 434 of the well 432 and running along the operational longitudinal direction 1 and through the lower body hub top 412. The bottom surface 434 of the well 432 can be flat, contoured, angled, undulated, etc. In some embodiments, at least a portion of the bottom surface 434 of the well 432 can be angled so that at least a portion of the bottom surface 434 slopes upward toward the lower body needle aperture 420. In other embodiments, the entire bottom surface 434 of the well 432 is angled so that the bottom surface 434 slopes downward in a radial direction away from the lower body needle aperture 420 all the way around the lower body needle aperture 420 (see FIG. 6A). In further embodiments, the bottom surface 434 has varying slopes and angles along the bottom surface 434. The sloped bottom surface 434 can be used to trap the needle tip 250 within the well.

As shown in FIG. 6B, the well 432 can be formed by a bore that is offset from the lower body needle aperture 420. In this embodiment, the bore need not be cylindrical and/or have a diameter that is greater than the diameter of the lower body needle aperture 420. Thus, the bore can be of any shape and/or diameter that enables the needle tip 250 to at least partially slide into a region of the well 432 so that the needle tip 250 becomes misaligned with the lower body needle aperture 420 and/or the needle tip 250 engages a portion of the well 432. Further, the well 432 and/or the bottom surface 434 of the well 432 may only be formed on one side of the lower body needle aperture 420. For example, and as a non-limiting example, the well 432 in FIG. 6B is formed on a front side of the lower body needle aperture 420.

A needle barrier 433 may separate the well 432 from the lower body needle aperture 420. In some embodiments, the needle barrier 433 can form part of the well 432 and part of the lower body needle aperture 420. The needle barrier 433 can be any size, shape, thickness, etc. In some embodiments, the needle barrier 433 can be part of the bottom surface 434. For example, the needle barrier 433 can form at least part of the slopped bottom surface 434, as shown in FIG. 6B.

Figure 6C:
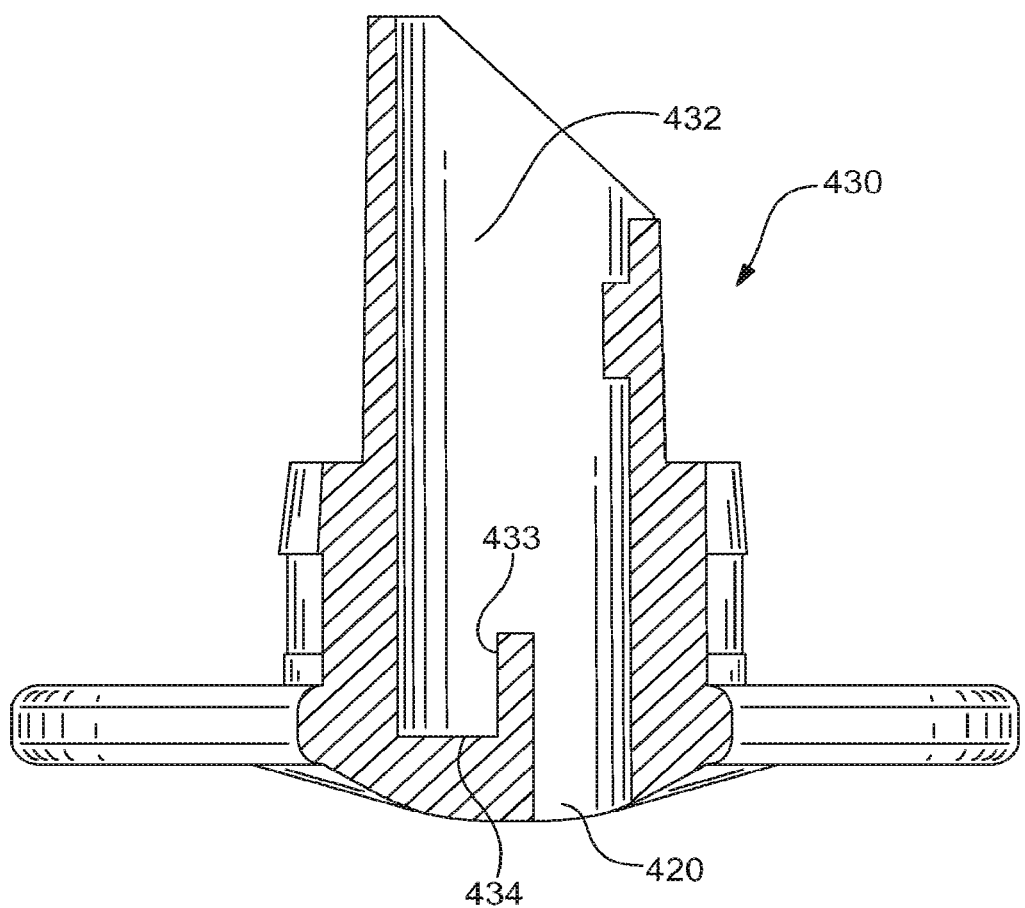
FIG. 6C is a close-up side cross-sectional view taken alone the A-A line of the Huber needle assembly with a well having a flat bottom only at one side of the needle aperture.
Figure 7A:
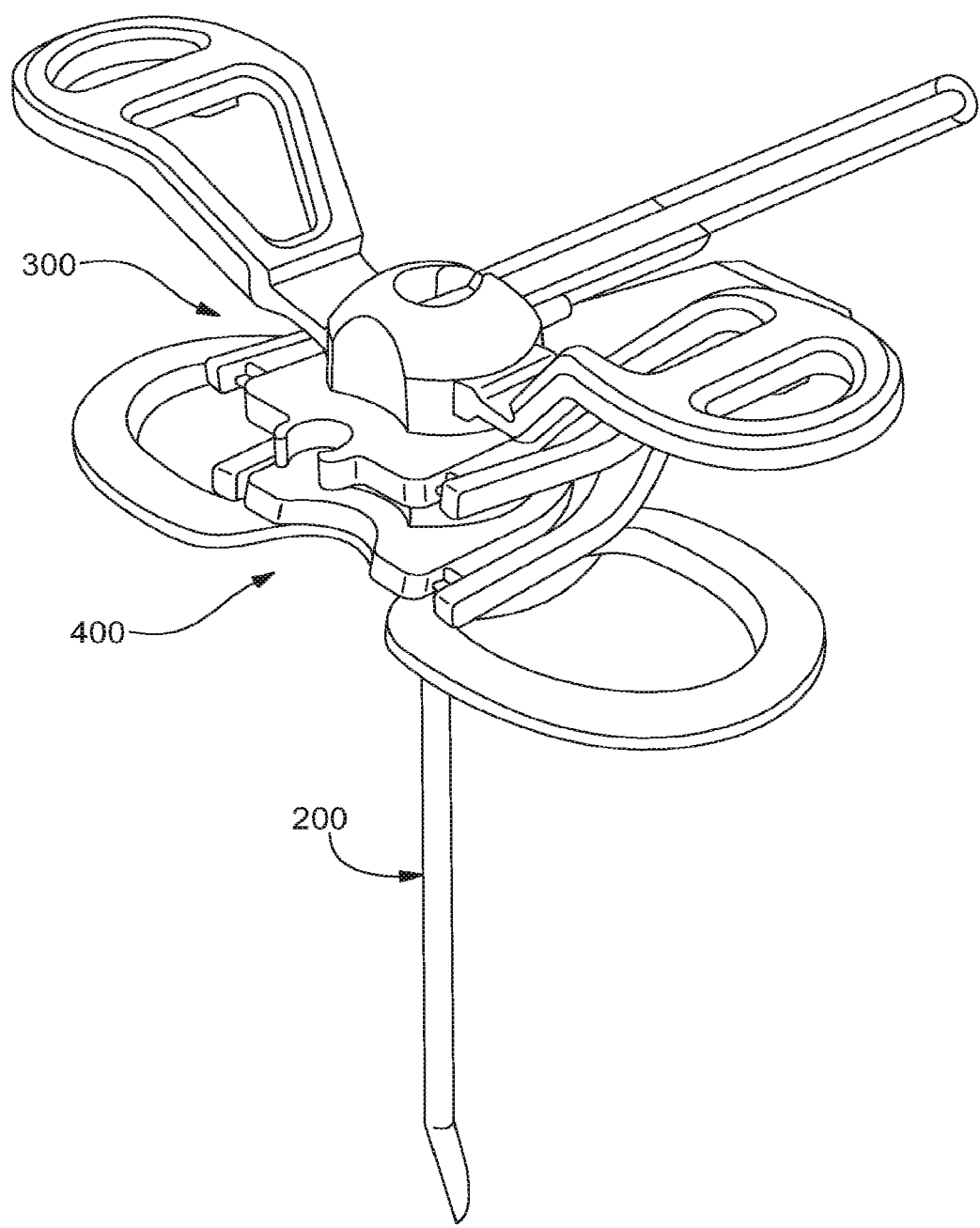
FIGS. 7A-7G show the Huber needle assembly being transitioned from a fully closed position to a fully open position, where
Figure 7B:
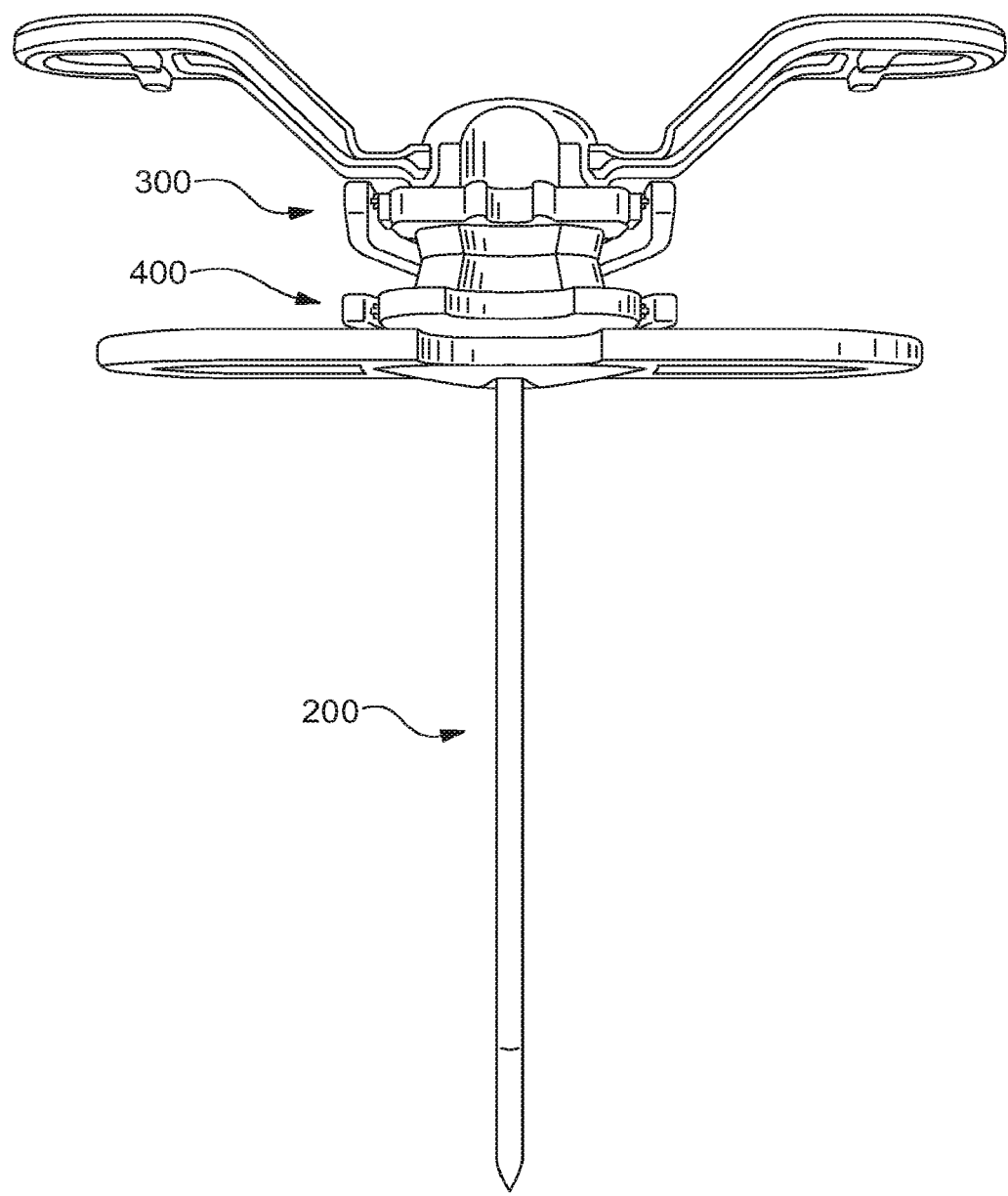
Figure 7C:
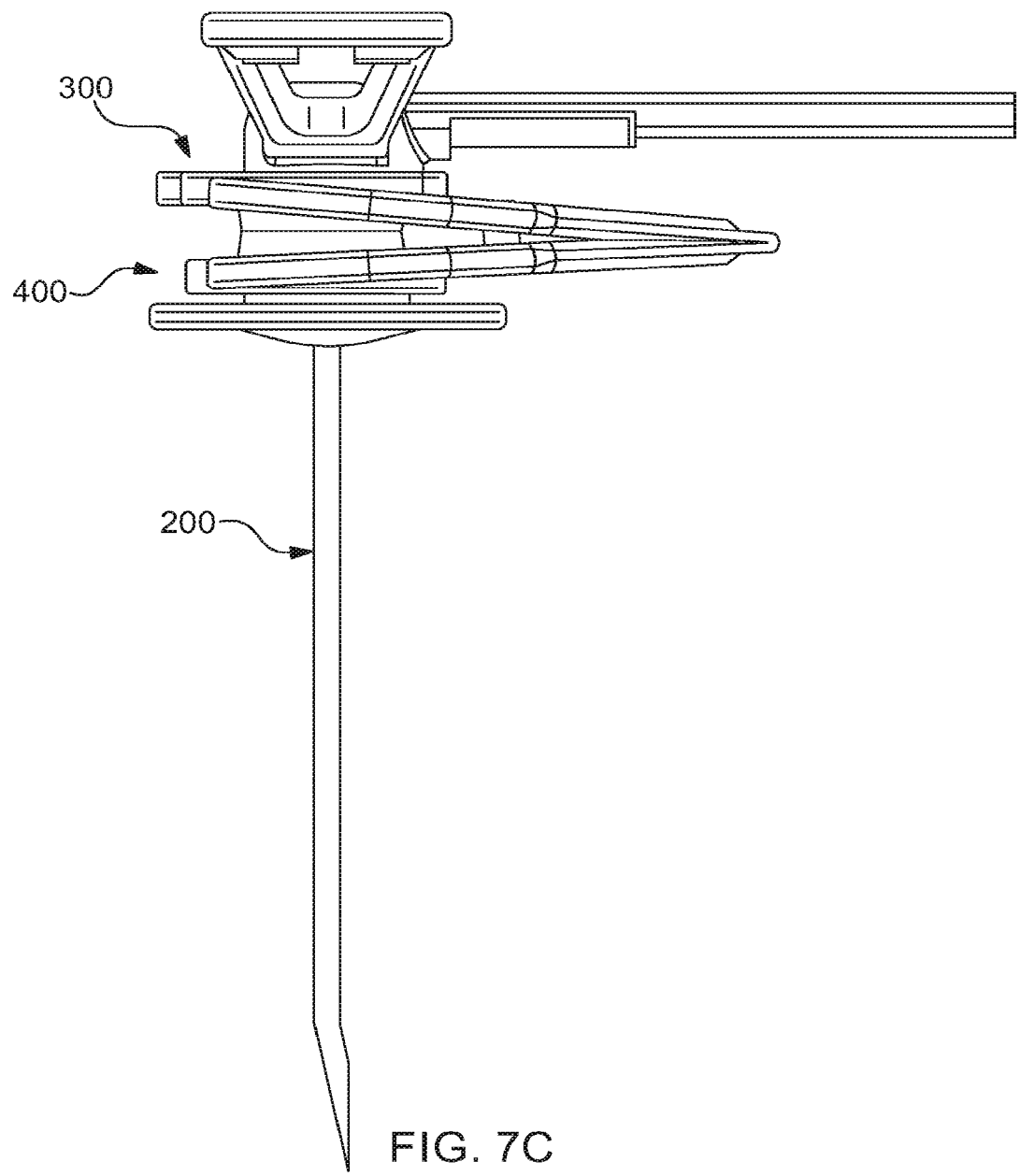
Figure 7D:
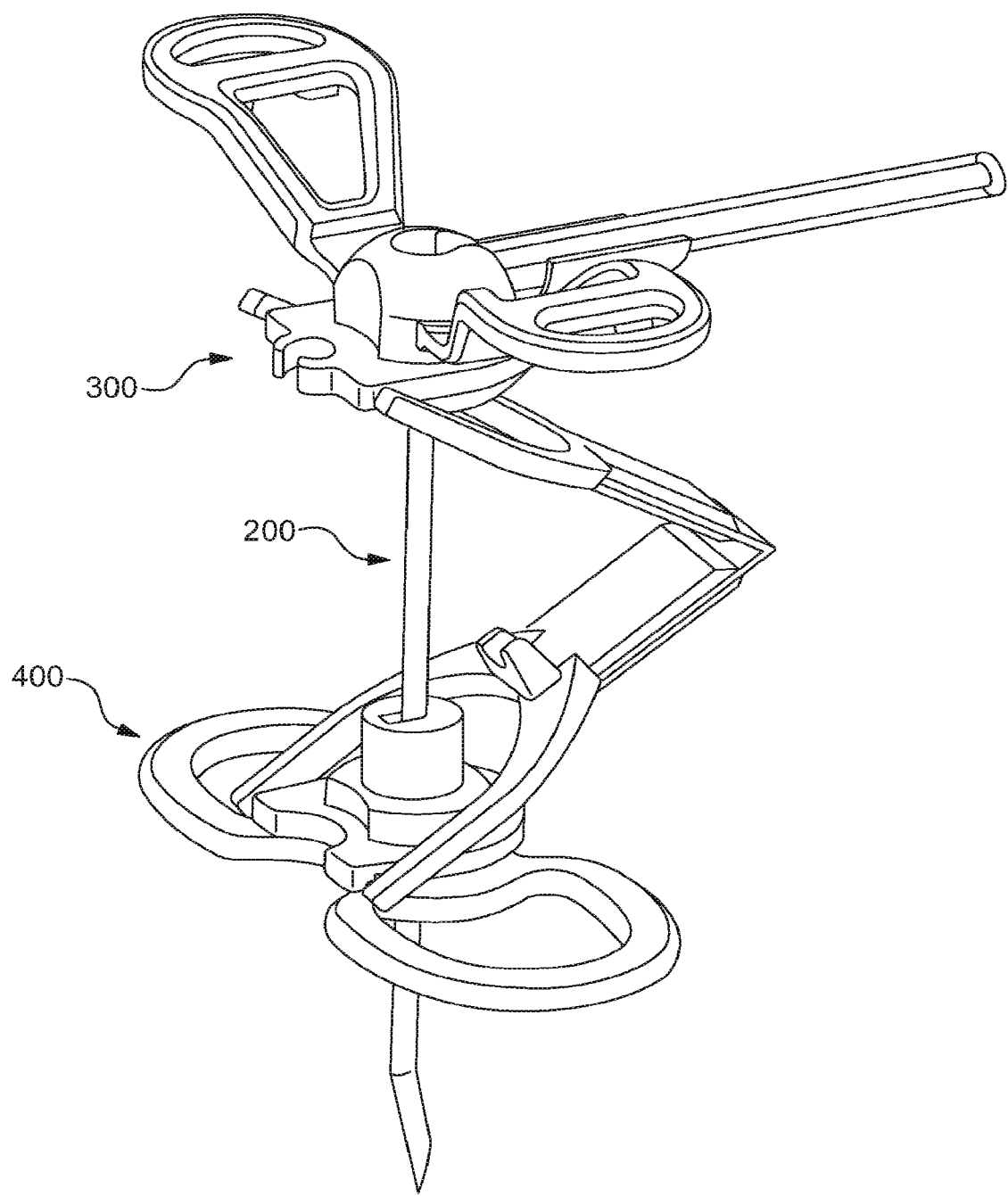
Figure 7E:
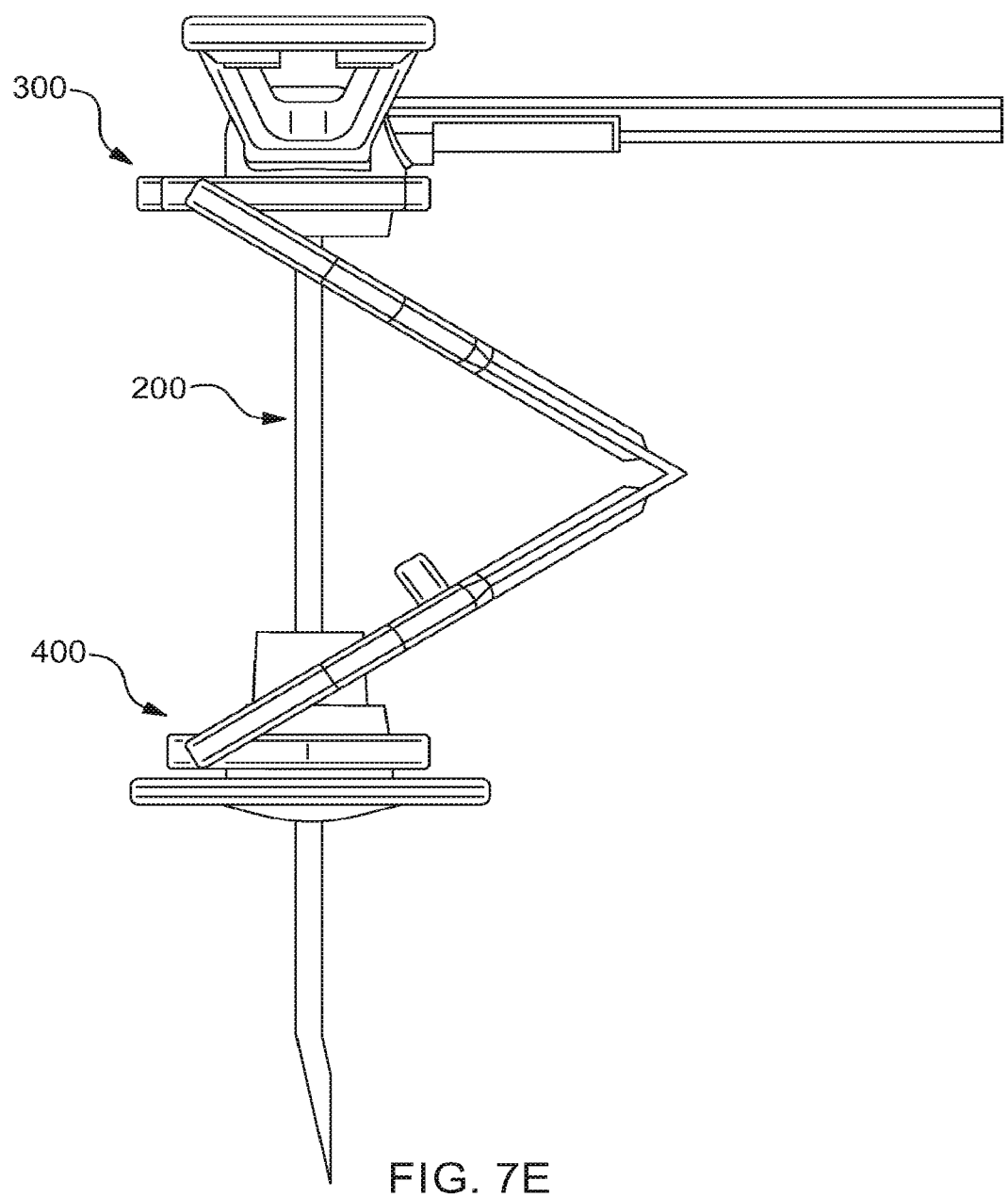
Figure 7F:
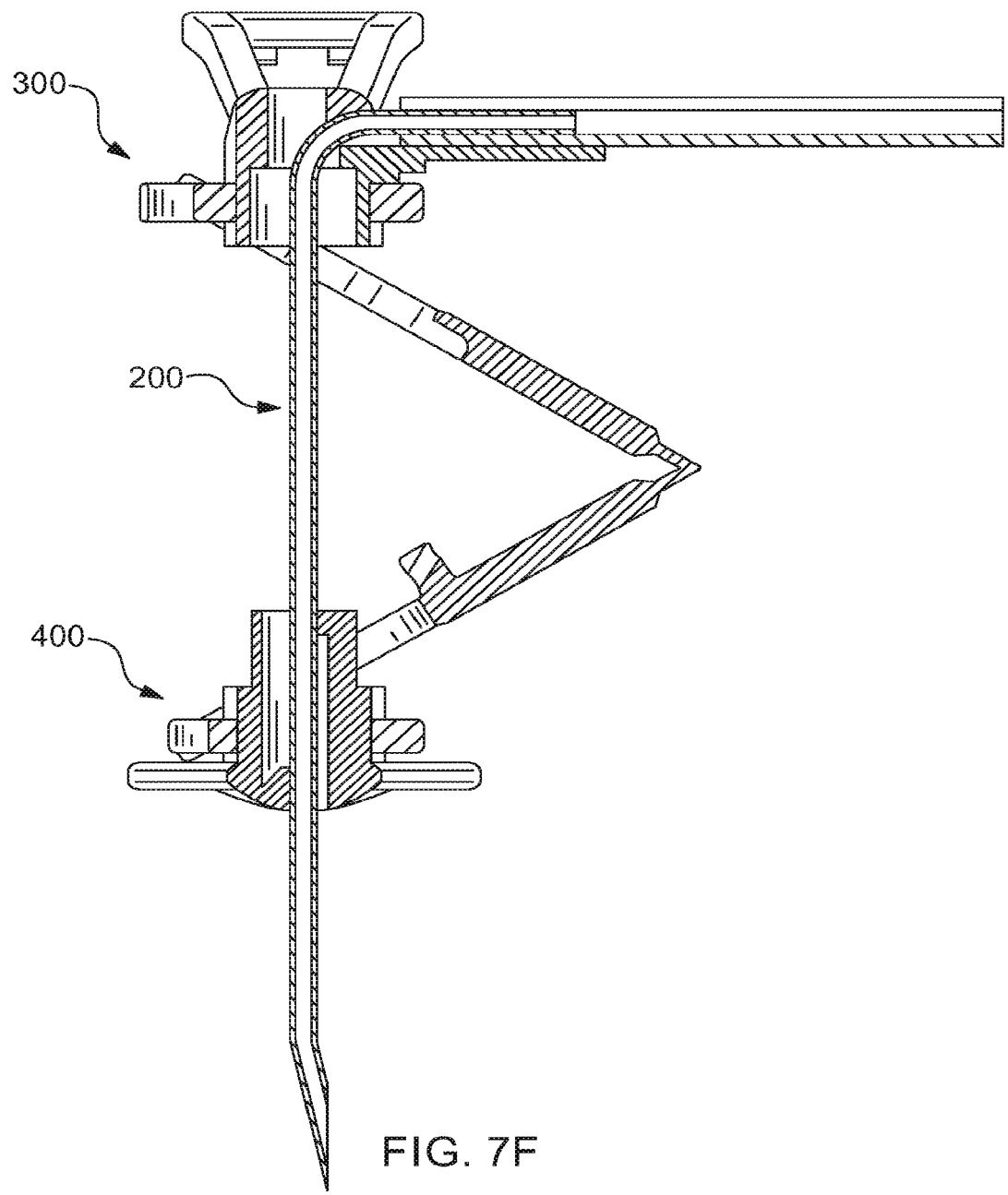
Figure 7G:
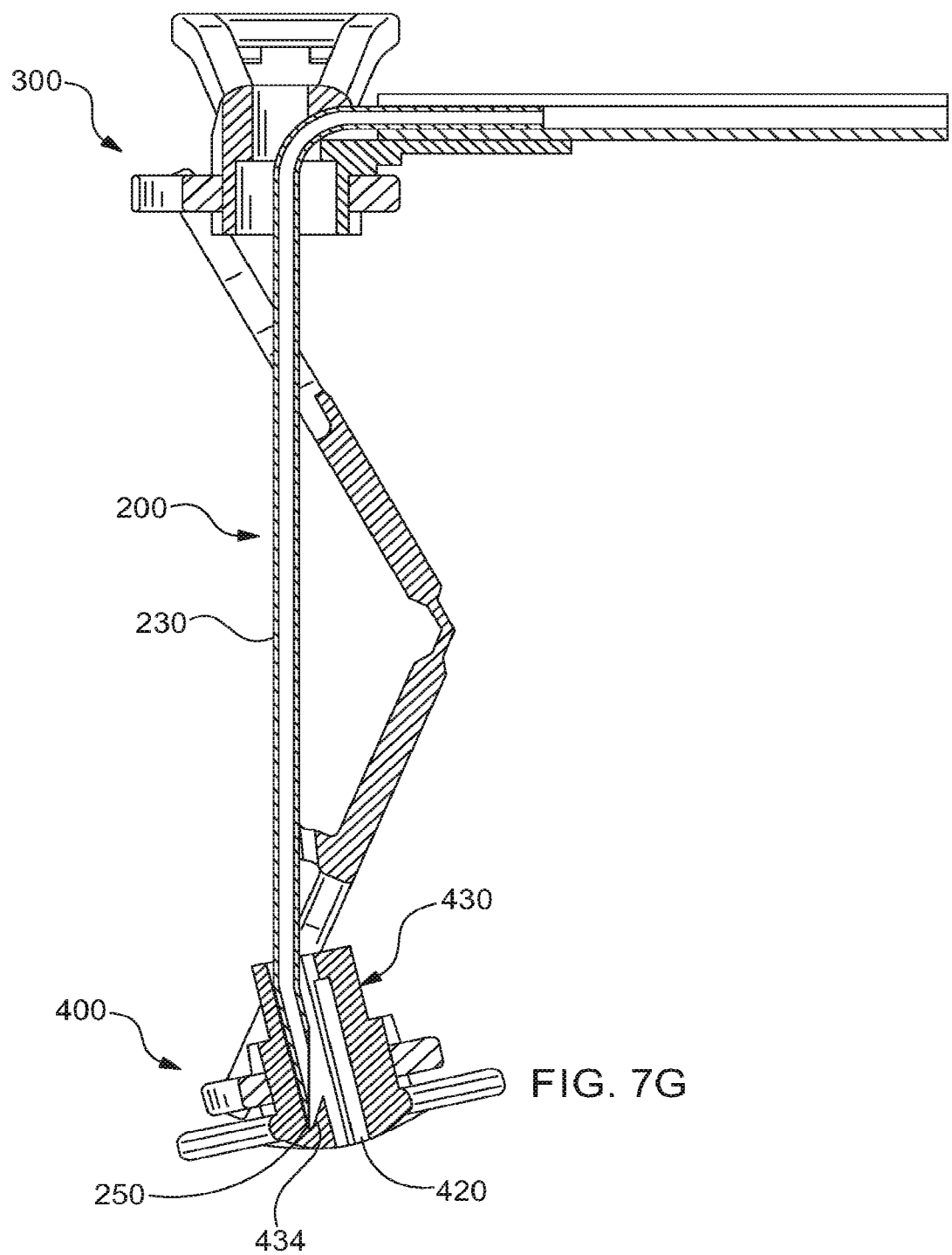
Figure 8A:
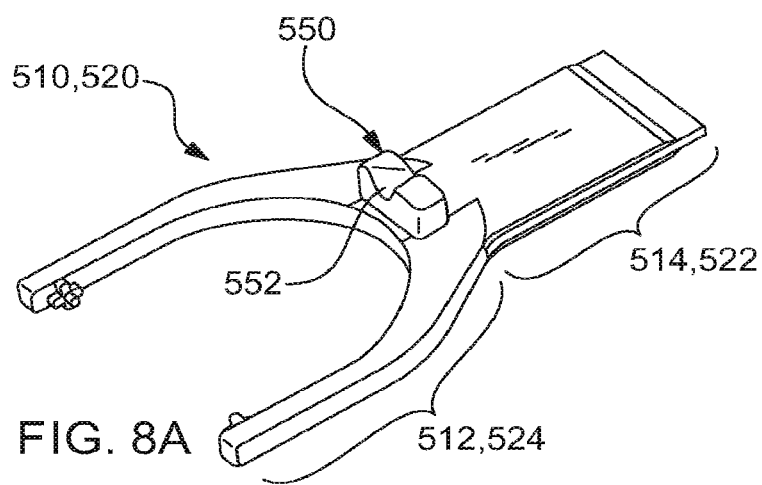
FIGS. 8A-8D are various views of a connector portion that may be used with a connector of a Huber needle assembly.
Figure 8B:
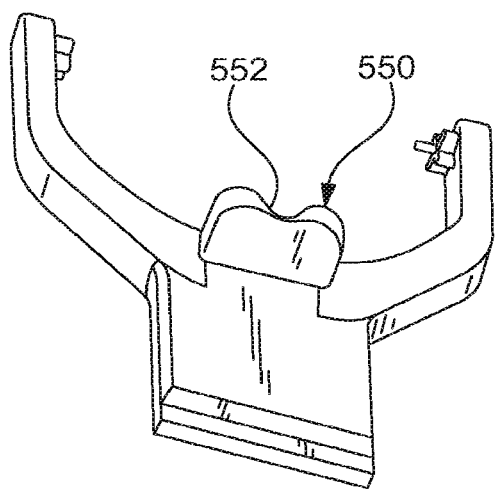
Figure 8C:
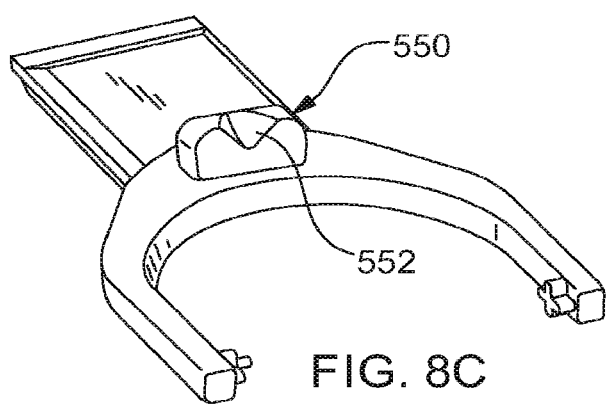
Figure 8D:
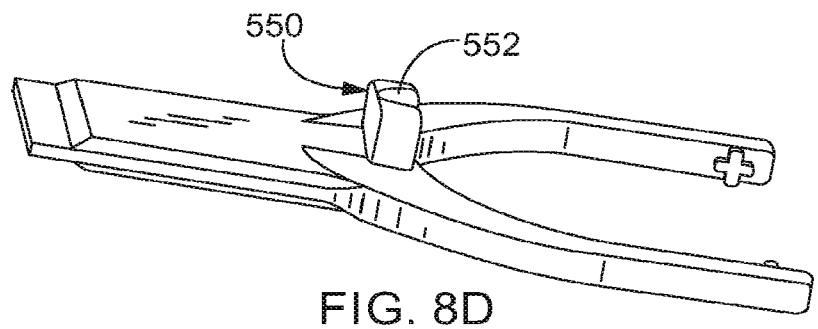
Figure 9A:
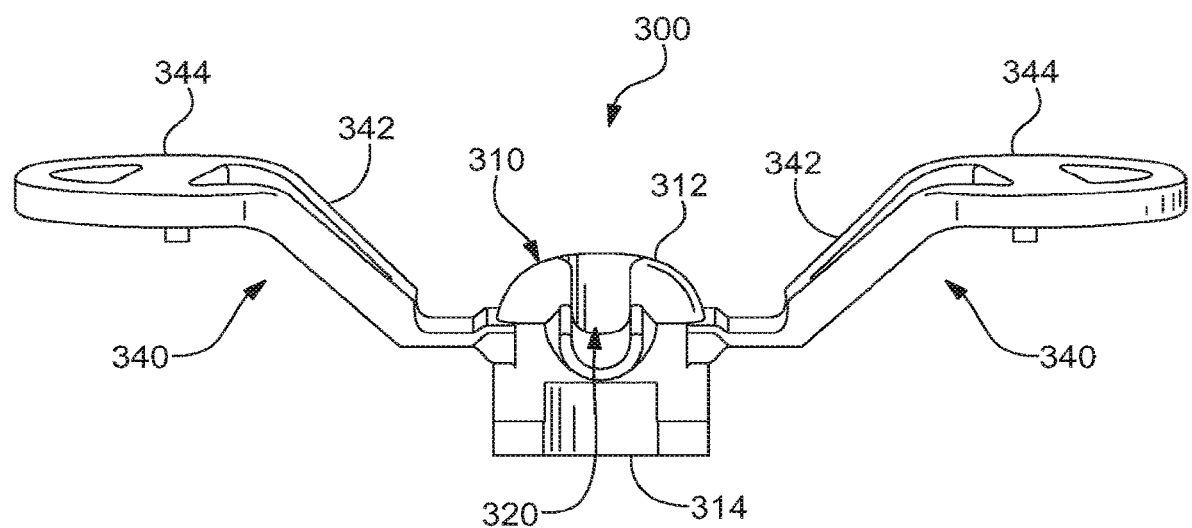
FIGS. 9A-9D are a rear view, a front view, a top view, and a bottom view, respectively, of an upper body that may be used with a Huber needle assembly.
Figure 9B:
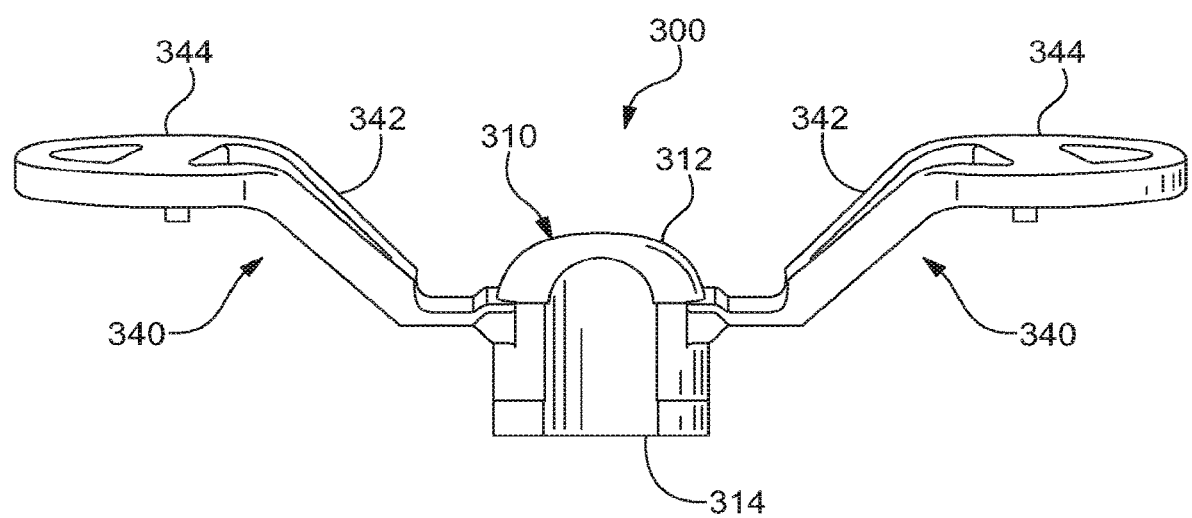
Figure 9C:
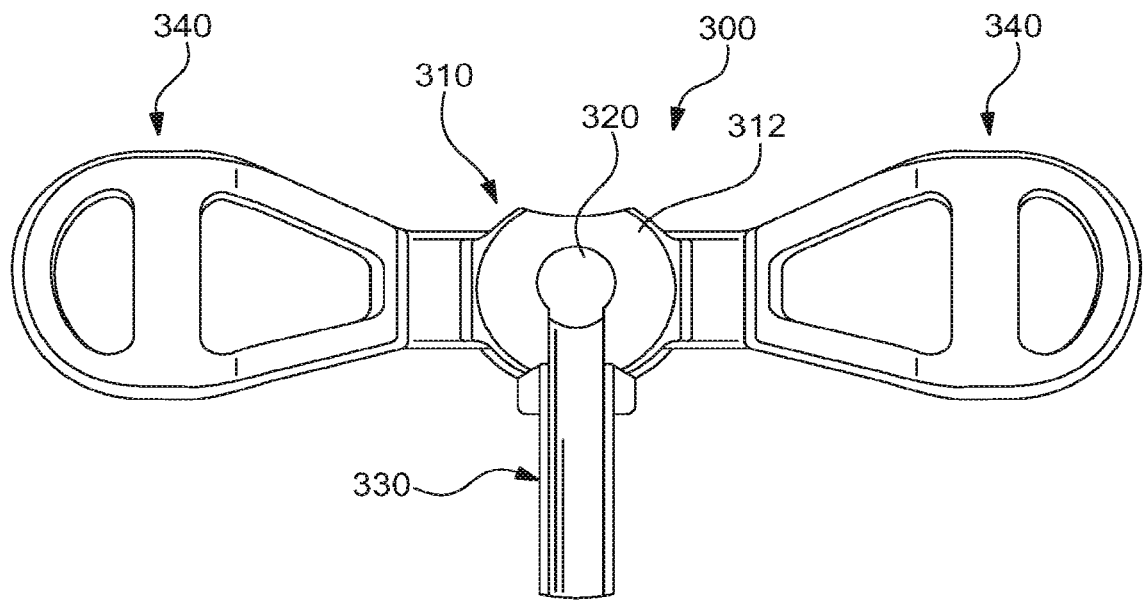
Figure 9D:
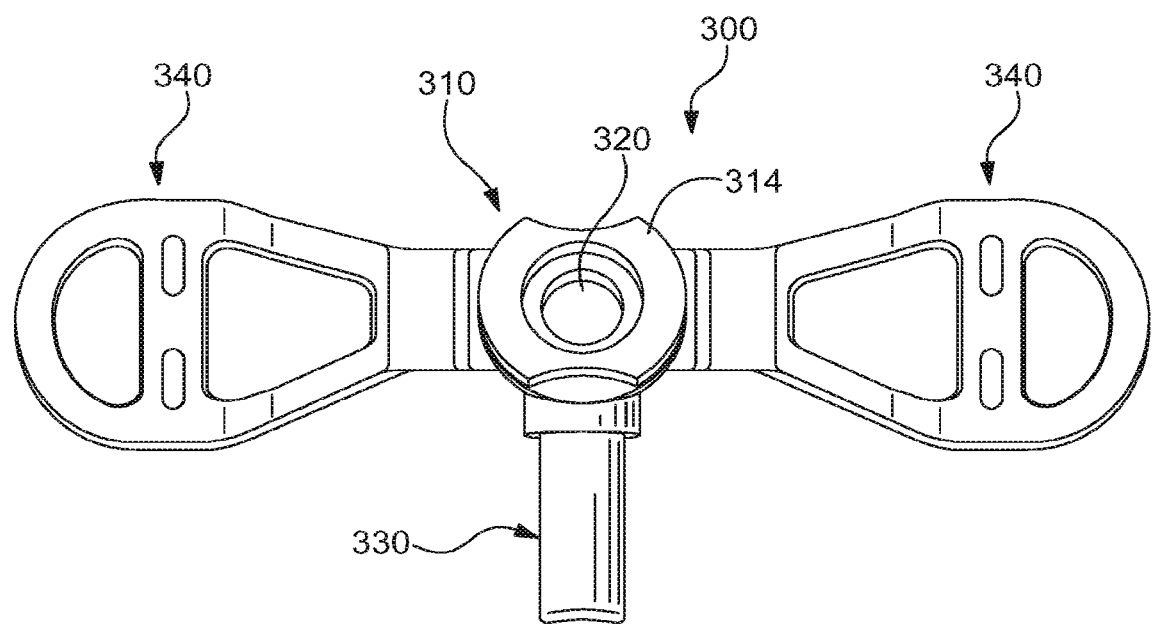
Figure 10A:
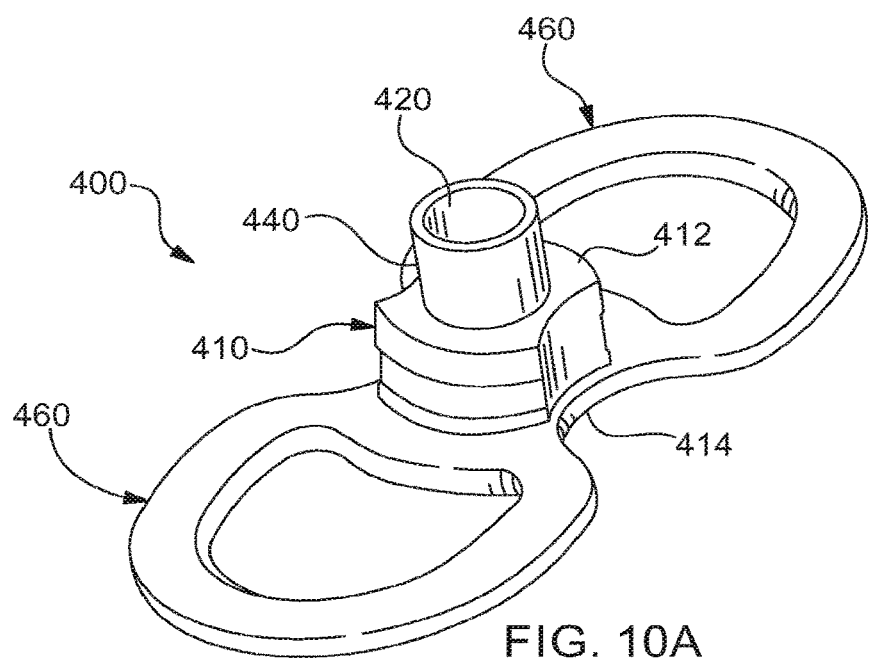
FIG. 10A-10F are a perspective view, a front/rear view, a bottom view, another bottom view, a top view, and another top view, respectively, of a lower body that may be used with a Huber needle assembly.
Figure 10B:
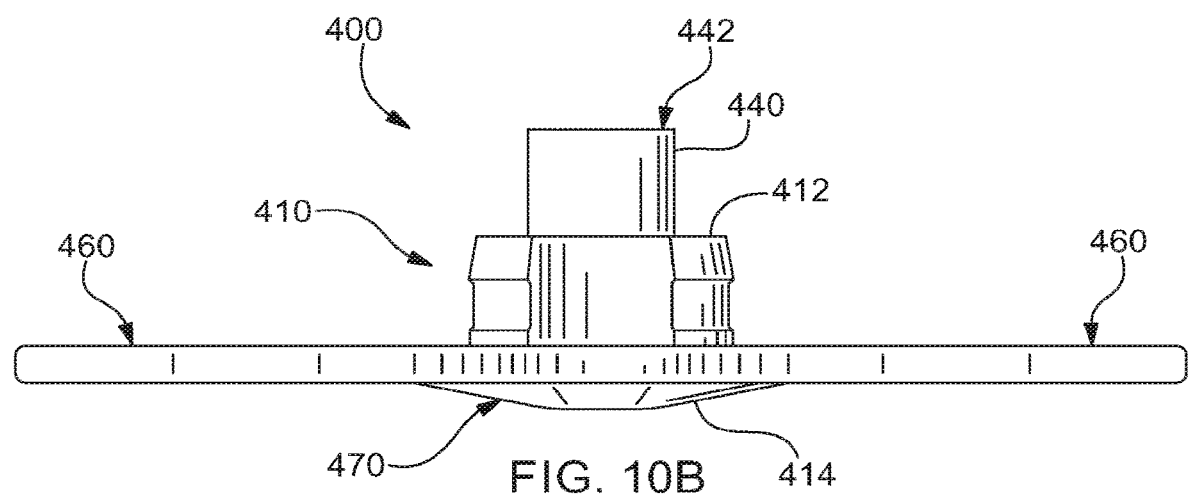
Figure 10C:
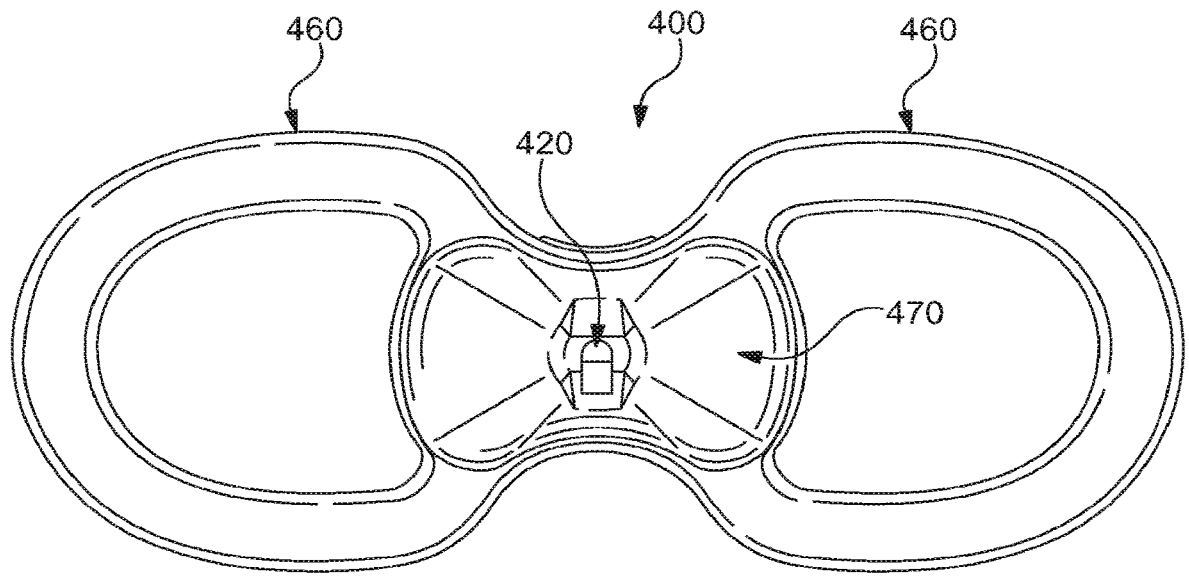
Figure 10D:
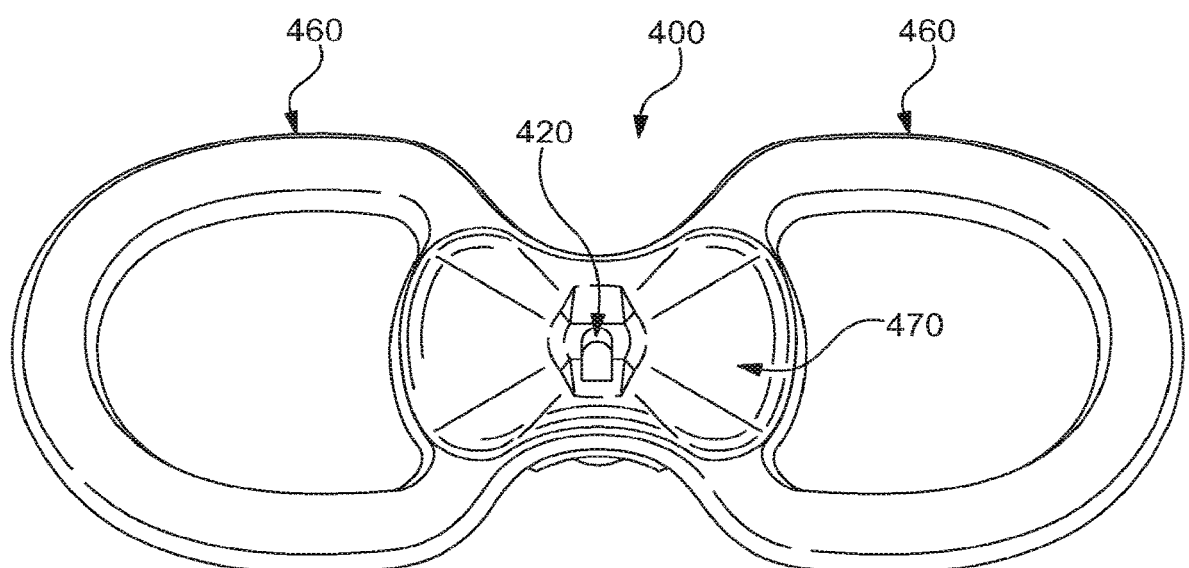
Figure 10E:
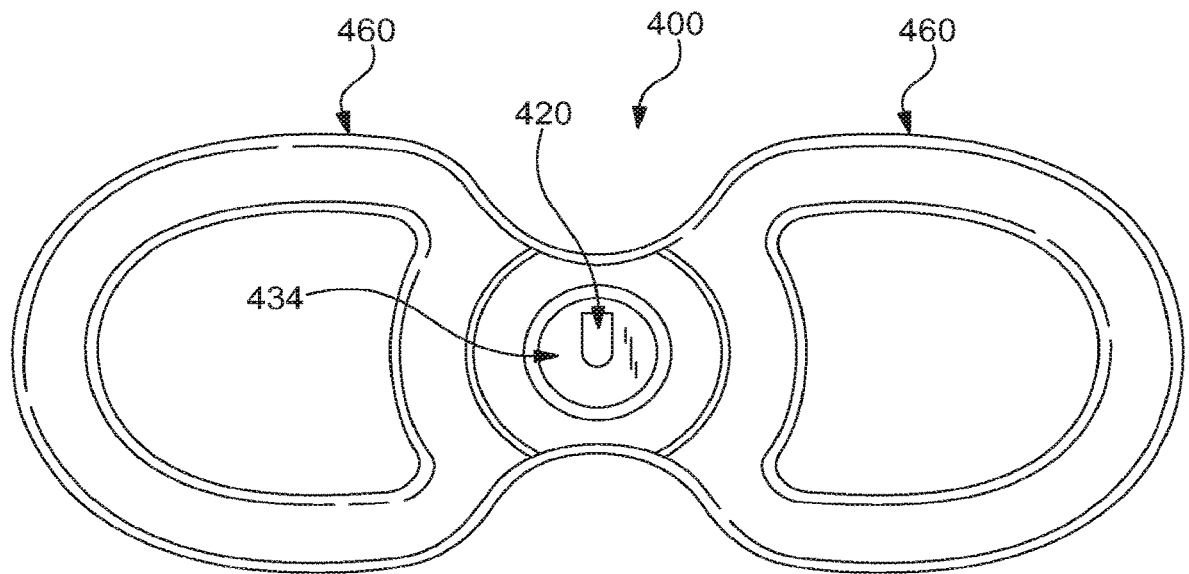
Figure 10F:
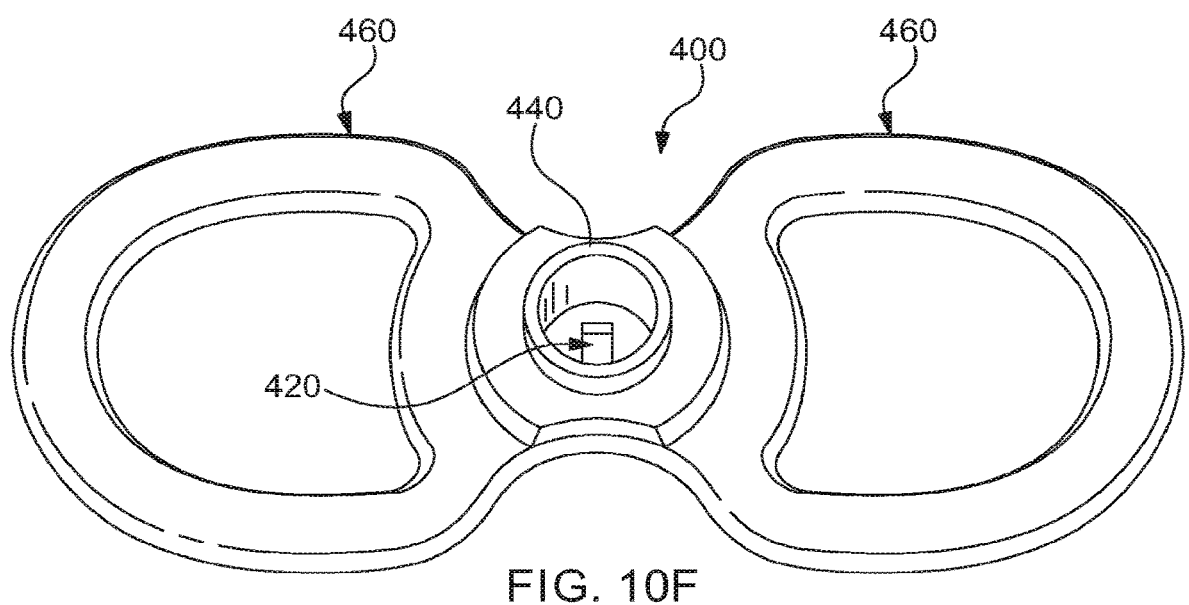

Referring to FIG. 6C, the well 432 can include a flat bottom surface 434. In some embodiments, well 432 and/or the flat bottom surface 434 of the well 432 can be formed all the way around a perimeter of the needle aperture 420. FIG. 6C shows an exemplary embodiment, where the well 432 and/or the flat bottom surface 434 of the well 432 can be formed on one side of the lower body needle aperture 420. For example, the well 432 in FIG. 6C is formed on a front side of the lower body needle aperture 420. The well 432 can be separated from the lower body needle aperture 420 by the needle barrier 433. The well 432 configuration of FIG. 6C may, in some embodiments, provide more room for the needle 200 and/or the needle tip 250 to be captured in the well 432. For example, the well 432 with the flat bottom surface 434 being on the front side of the lower body needle aperture 420 can provide more room for the needle tip 250 to move to the lowest point of the well 434. In other words, the configuration of FIG. 6C, in some embodiments, can provide more room to capture the needle tip 250 at the lowest point.

The lower body hub top 412 can include a flange extension 440. The flange extension 440 can be a member that extends from the lower body hub top 412. The flange extension 440 can be positioned adjacent the bore. The flange extension 440 can be a partially cylindrical member, a semi-circular cylindrical member, or a full cylindrical member disposed around the bore. Further, the flange extension 440 can take other shapes, such as a square, triangle, chevron, etc. The volume of space defined by the flange extension 440 and the catch 430 can form the enveloping structure 450. In other words, the volume of space extending from the bottom surface 434 of the well 432 to flange extension top 442 is confined by the combined structure of the flange extension 440 and the catch 430 and thus can form the enveloping structure 450.

It is envisioned for the assembly 100 to be packaged and shipped in a "ready-to-use" state. Use of the assembly 100 would begin with the assembly 100 in the fully closed position, and thus it is envisioned to package and ship the assembly 100 in the fully closed position. However, the assembly 100 can be used starting out in any position, and thus the assembly 100 can also be packaged and shipped in any position. FIGS. 7A-7G illustrate the assembly 100 transitioning from a fully closed position to a fully open position. An exemplary use of the assembly 100 may include removing the assembly 100 from its packaging while the assembly is within its fully closed position (see FIG. 7A-7C). The needle 200 would then be inserted into the insertion site with the assembly 100 being maintained in the fully closed position. Treatment may then be supplied via the needle 200. After treatment, or when it is otherwise desired, the assembly 100 may be transitioned from the fully closed position to the safety-lock position (i.e., the fully open position). To transition the assembly 100 to the safety-lock position, the upper body 300 and the needle 200 can be caused to move relative to the lower body 400, facilitating withdraw of the needle tip 250 from the insertion site (see FIGS. 7D-7F). This can be achieved by stabilizing the lower body 400 with a first hand (e.g., applying pressure to one or both of the stabilization plates 460 and/or grasping one or both of the stabilization plates 460) and grasping one or both of the handle(s) 340 of the upper body 300 with a second hand, and then pulling the upper body 300 away from the lower body 400 along the operational longitudinal direction 1. Alternatively, a user can grasp any portion of the lower body 400 to stabilize it and grasp any portion of the upper body 300 to cause it to move relative to the lower body 400. As the upper body 300 is further moved away from the lower body 400, the needle tip 250 can withdrawal from the insertion site and retract into the lower body aperture 420. For example, the needle tip 250 can be forced to move above the lower body hub bottom 410 and be pulled within the lower body 400 towards the well 432. Moving the upper body 300 further away from the lower body 400 can cause the needle tip 250 to be withdrawn into a portion of the enveloping structure 450. Once within the enveloping structure 450, the assembly 100 can transition to the safety-lock position or the fully open position (see FIG. 7G).

In some embodiments, the connector 500 can be structured so as to be fully extended when the needle tip 250 is withdrawn into the enveloping structure 450, and thus no further movement of the upper body 300 away from the lower body 400 can be achieved. For example, the connector 500 can be structured so as to cease movement of the upper body 300 away from the lower body 400 so that the needle tip 250 does not extend beyond the flange extension top 442. In further embodiments, the connector 500 can be structured so as to be fully extended when the needle tip 250 is withdrawn into the well 432, and thus no further movement of the upper body 300 away from the lower body 400 can be achieved. For example, the connector 500 can be structured so as to cease movement of the upper body 300 away from the lower body 400 so that the needle tip 250 does not extend beyond a top 436 (see FIG. 6B) of the well 432 or beyond the upper body hub top 412.

The catch 430 can be used to engage the needle tip 250 once the needle tip 250 has been retracted into a portion of the enveloping structure 450. Engagement between the catch 430 and the needle tip 250 can cause the assembly 100 to transition into the safety-lock position. For example, once the needle tip 250 has been retracted into a portion of the enveloping structure 450, the needle tip 250 can be caused to engage the bottom surface 434 of the well 432 (e.g., the needle tip 250 abuts the bottom surface 434 of the well 432), thereby arresting any movement of the needle 200 and/or upper body 300 towards the lower body 400. In the safety-lock position, the enveloping structure 450 can envelope the needle tip 250, and thus the assembly 100 can prevent movement of the needle tip 250 from inside the volume of space within enveloping structure 450, effectively sheathing the needle tip 250 so as to prevent any type of exposure of the needle tip 250 to an environment outside of the enveloping structure 450. Further, while the lower body needle aperture 420 has a diameter that is larger than the needle 200, it is not so large to allow a user to insert a finger or other body portion therein. Thus, in a safety-lock position, the enveloping structure 450 can prevent any type of exposure to the needle tip 250. Further, in the safety-lock position, the needle tip 250 is misaligned with the lower needle aperture 420, thereby preventing rebound. For example, when the needle tip 250 is within the well 432 and misaligned with the lower needle aperture 420, the needle tip 250 cannot be moved through the lower needle aperture 420 and thus cannot be protrude through a bottom of lower body 400. Further, when the needle tip 250 is within the well 432, misaligned with the lower needle aperture 420, and is engaged with a portion of the well 432, the needle tip 250 cannot be moved through the lower needle aperture 420 to protrude through the bottom surface 434 of the well 432. It is noted that a mere misalignment of the needle tip 250 with the lower body needle aperture 420 can be enough to place the assembly 100 in a safety-lock position. Thus, it is not necessary for the needle tip 250 to engage a portion of the well 432 to generate a safety-lock position.

Figure 3:
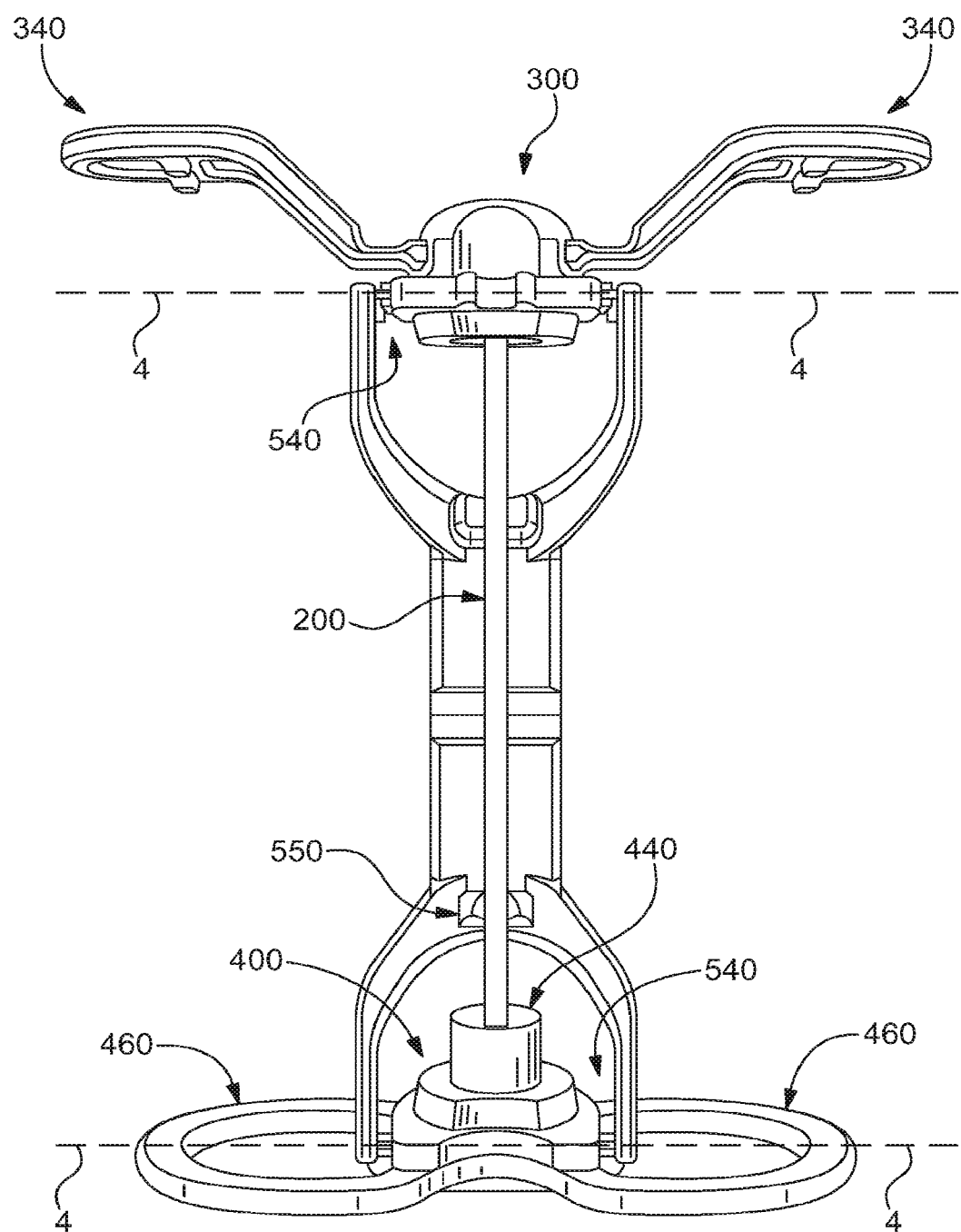
FIG. 3 is a front view of the Huber needle assembly.
Figure 5:
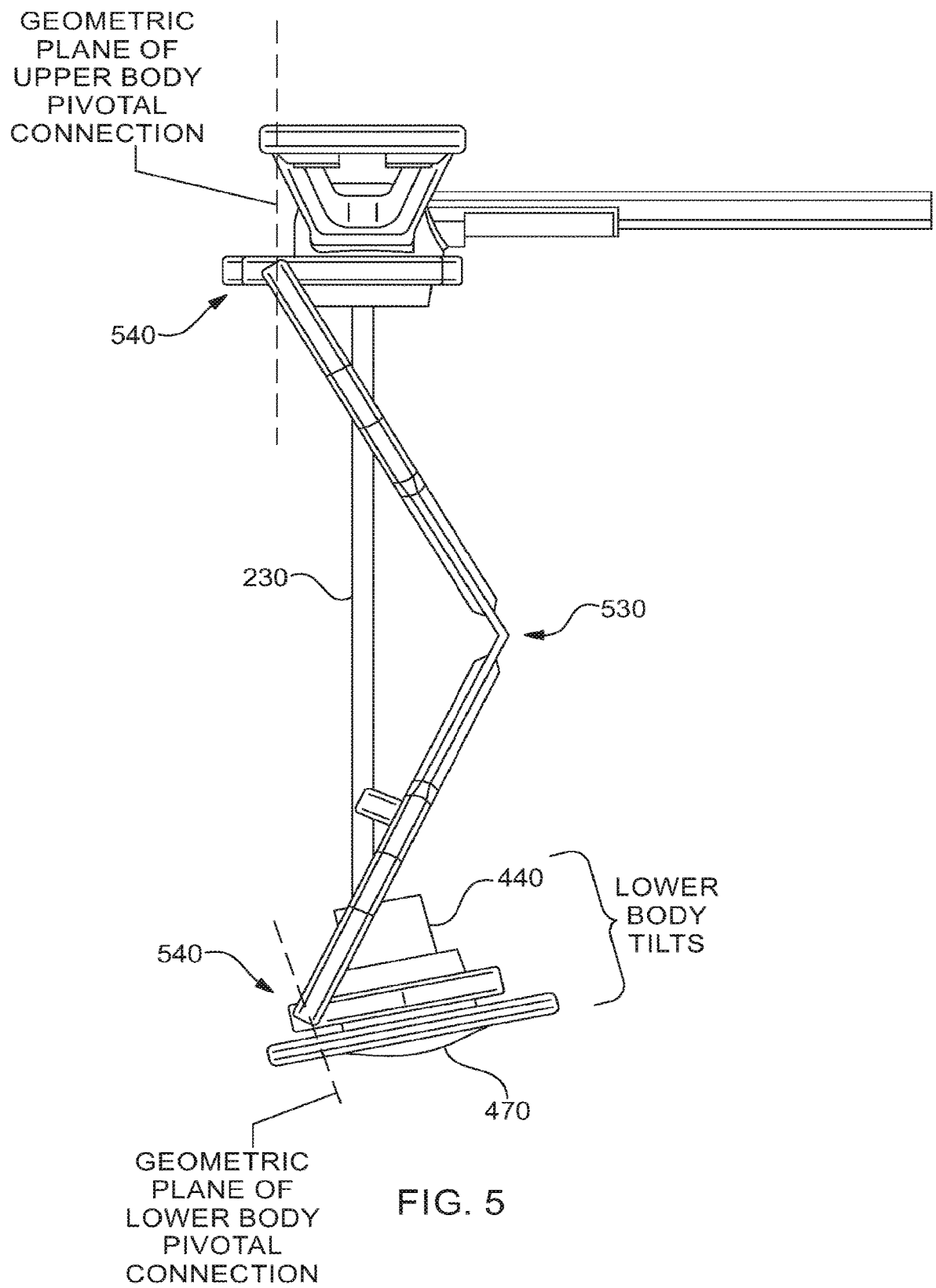
FIG. 5 is a side view of the Huber needle assembly in a safety-lock position.

Referring back to FIGS. 4-5, in some embodiments, at least one of the pivot connections 540 can facilitate swivel motion of the upper body 300 and/or lower body 400 about a pivot connection axis 4 (see FIG. 3). As shown in FIGS. 4-5, and as a non-limiting example, the lower body 400 swivels or tilts at an angle to accommodate misalignment of the needle tip 250 with the lower body needle aperture 420 and/or engagement of the needle tip 250 with a portion of the well 432. FIG. 4 shows the lower body 400 without exhibiting a tilt while the assembly 100 is in a non safety-lock position, and FIG. 5 shows the lower body 400 exhibiting a tilt while the assembly 100 is in a safety-lock position.

Causing misalignment of the needle tip 250 with the lower body aperture 420 and/or causing engagement of the needle tip 250 with the catch 430 can be achieved in various ways. For example, the advancing assist 550 may be used to make contact with or engage the needle shaft 230 as the upper body 300 is moved away from the lower body 400, urging the needle shaft 230 in the forward operational latitudinal direction 3b as the upper body 300 is further moved away from the lower body 400. This may cause the needle tip 250 to misalign with the lower body needle aperture 420 once the needle tip 250 is withdrawn into a portion of the enveloping structure 450 and/or facilitate the needle tip 250 engaging a portion of the well 432. As another example, the offset of any one or both of the geometric planes of the upper body pivotal connection 540 and the lower body pivotal connection 540 with respect to the axis of the operational longitudinal direction 1 can cause the needle tip 250 to be urged in the forward operational latitude direction 3b as the upper body 300 is moved away from the lower body 400. This may cause the needle tip 250 to misalign with the lower body needle aperture 420 once the needle tip 250 is withdrawn into the enveloping structure 450 and/or facilitate the needle tip 250 engaging a portion of the well 432. As another example, the movement of the upper body 300 away from the lower body 400 can cause the needle tip 250 to enter the well 432 where misalignment of the needle tip 250 with the lower body needle aperture 420 allows the needle tip 250 to make contact with the sloped bottom surface 434 of the well 432, causing the needle tip 250 to slide into a depression formed into a bottom of the well 432. This may trap the needle tip 250 within the well, preventing the needle tip 250 from moving in the operational latitudinal direction 2 after the needle tip 250 has engaged the well 432. Further, when the needle tip 250 is trapped, the connector 500 can be structured to be at or near its fully extended position, thus the needle tip 250 would be further prevented from moving in a direction away from the lower body 400. Therefore, the configuration can ensure that the needle tip 250 is trapped within the well 432 and/or misaligned with the lower body needle aperture 420.

In at least one embodiment, the lower body 400 can tilt as the upper body 300 is cause to be moved away from the lower body 400. (See FIGS. 6A-6B). This may cause the needle tip 250 to misalign with the lower body needle aperture 420 once the needle tip 250 is withdrawn into the enveloping structure 450 and/or facilitate the needle tip 250 engaging a portion of the well 432. The assembly may be structured such that the tilting urges the needle tip 250 in the forward operating direction 3b, and thus cause it to misalign with the lower body needle aperture 420 and/or engage a portion of the well 432. For example, a rear portion of the lower body 400 well 432 may make contact with a rear surface of the needle 200 (see FIG. 6B), as the lower body 400 tilts. This can cause the needle to be urged in the forward operational direction 3b, which may further cause the needle tip 250 to misalign with the lower body needle aperture 420 and/or engage a portion of the well 432. Alternatively, the mere tilting of the lower body 400 as the upper body 300 moves away from the lower body 400 can cause the needle tip 250 to misalign with the lower body needle aperture 420 and/or engage a portion of the well 432 without the needle 200 being urged in the forward operational direction 3b. In other words, the tilting of the lower body 400 may merely move the lower body needle aperture 420 away from alignment of the needle tip 250. In other embodiments, the tilting of the lower body 400 both: 1) causes the needle tip 250 to misalign with the lower body needle aperture 420 and/or engage a portion of the well 432; and 2) urges the needle 200 in the forward operational direction 3b to ensure that the needle tip 250 misaligns with the lower body needle aperture 420 and/or engages a portion of the well 432.

As discussed above, any of the methods disclosed herein for urging the needle shaft 230 in a desired direction as the assembly 100 is transitioned from the closed position to the open position can be referred to as biasing the needle 200 and/or needle tip 250 away from the lower body needle aperture 420. This can cause the needle 200 and/or needle tip 250 to misalign with the lower body needle aperture 420 and/or cause the needle tip 250 to engage a portion of the catch 430. Alternatively, or in addition, biasing the needle 200 and/or needle tip 250 can also prevent re-alignment of the needle 200 and/or needle tip 250 with the lower body needle aperture 420. In any event, biasing the needle 200 and/or needle tip 250 in a direction can prevent re-emergence of the needle tip 250 from an interior space of the lower body 400, which may include re-emergence from the well, 432, the catch 430, and/or the enveloping structure 450. Other methods of biasing the needle 200 and/or needle tip 250 can include but are not limited to, use of a spring, spring-pin tumbler, elastic member, a cam assembly, etc. For example, a spring (e.g., coil spring, leaf spring, extension spring, etc.) can be positioned within the enveloping structure 450 and/or placed on a portion of the connector 500 and structured to impose a force on a portion of the needle 200 to urge the needle 200 and/or needle tip 250 in a desired direction. This direction can be in the forward operational latitudinal direction 3b, for example. The spring can be structured to apply a continuous force on a portion of the needle 200 so as to always bias the needle 200 and/or needle tip 250 in the desired direction or only impose a force on a portion of the needle 200 when the assembly is transitioning into the fully open position. For example, the spring can be positioned within the well 432 to continuously urge the needle 200 and/or needle tip 250, regardless of whether the assembly is in a close position, an open position, or any intermediary position. As another example, the spring can be placed on a portion of the connector 500 so as to only impose a force on the needle 200 when making contact with the needle 200. Thus, only during a transitioning into the open position will the spring impose a force on the needle 200.

In a preferred embodiment, the needle 200 may be statically affixed to the upper body 300, and thus biasing and/or urging the needle in the forward operational direction can refer to causing the lower body 400 to move relative to the needle 200 and/or upper body 300. For example, as the upper body 300 is caused to move relative to the lower body 300, the lower body 400 may tilt, thereby moving relative to the needle 200 and/or upper body 300. This relative motion can cause the misalignment of the needle 200 and/or needle tip 250 with the lower body needle aperture 420 and/or cause the needle tip 250 to engage a portion of the catch 430.

Further embodiments can include various shapes exhibited by the well 432. For example, the well 432 can have a cylindrical drum shape, a cube shape, a pyramidal shape, etc. In addition, any surface of the well 432 can have undulating, stepped, teethed, notched, etc. surfaces. For example, a stepped side surface can be used to engage the needle tip 250 in addition to, or in the alternative to, the bottom surface 434 of the well 432. Some embodiments can include a soft material (e.g., rubber) coating or disposed on at least a portion of a surface of the well 432. The soft material may be used to engage the needle tip 250 by allowing the needle tip 250 to stick into soft material.

Further embodiments can include configuring the well 432 so that when the needle tip 250 engages a portion of the well 432, an audible sound emanates therefrom. For example, as seen in FIGS. 6A-B, the bottom surface of the 16a well 432 can exhibit a steep slope (e.g., at least 60 degrees). Thus, when the needle tip 250 is caused to withdraw back into the enveloping structure 450 and moved beyond a highest portion of the bottom surface 434 of the well 432, the needle 200 may be forced in the forward operational latitudinal direction 3a and/or toward the lower body 400 due to the configuration of the assembly 100, as described above. The urging of the needle 200 in the forward operational latitudinal direction 3a and/or toward the lower body 400 can cause the needle 200 to impact a portion of the well 432 to generate an audible sound (e.g., a snap sound). This audible sound can be used to provide positive feedback to a user that the assembly 100 has transitioned into the safety-lock position. Other means to generate the audible sound can be achieved such as, for example, providing a flat side surface of the well 432 that substantially conforms to an outer surface of the needle tip 250 so that impact with the side surface by the needle causes a snap sound.

In at least one embodiment, a location of the bottom surface 434 of the well 432 can be raised and/or the lower body 400 can be raised to close a distance between the lower body 400 and the upper body 300. Further, any one of the upper body and lower body needle apertures 320, 420 can be centered within its respective upper body 300 or lower body 400. Additionally, or in the alternative, any one of the upper body and lower body needle apertures 320, 420 can be off-centered within its respective upper body 300 or lower body 400. In some embodiments, the location of the bottom surface 434 of the well 432 can be raised and/or the lower body 400 can be raised to close a distance between the lower body 400 and the upper body 300, and any one of the upper body and lower body needle apertures 320, 420 can off-centered within its respective upper body 300 or lower body 400. This may facilitate smoother operation of the assembly 100. Further, such a configuration may allow for better alignment between the upper body and lower body 300, 400 and provide more room for the needle 200 (or at least the needle tip 250) to engage, or even get trapped into, a portion of the well 432 when the needle shaft 230 is urged in the forward operational latitudinal direction 3b.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. A Huber needle assembly, comprising:
   a needle comprising a needle shaft leading to a needle tip, wherein the needle extends in a first direction from a rear of the assembly to a front of the assembly, makes a 90-degree bend, and extends in a second direction toward a bottom of the assembly, wherein the second direction is along an axis of an operational longitudinal direction;
   an upper body having an upper body needle aperture formed therein;
   a lower body having a lower body needle aperture and a well, wherein the lower body needle aperture leads into at least a portion of the well, wherein a volume of space extending from a well bottom surface to a top of the lower body is an enveloping structure; and,
   a connector connecting the upper body to the lower body, the connector facilitating a movement of the upper body along the operational longitudinal direction and limiting a separation distance between the upper body and the lower body to prevent the needle tip from extending beyond the top of the lower body;
   wherein a movement of the upper body away from the lower body retracts the needle tip within the lower body through the lower body needle aperture and biases the needle away from the lower body needle aperture, wherein the needle is biased in an operational latitudinal direction via an advancing assist configured to, as the upper body moves away from the lower body, be forced to move from a first state of not contacting the needle to a second state of contacting or engaging the needle, and the advancing assist is disposed on a portion of the connector; and
   wherein the lower body tilts relative to the second direction of the needle shaft to facilitate an engagement of the needle tip with at least a portion of the well, whereby when the needle tip enters the portion of the well, the needle tip has a misalignment with the lower body needle aperture.

2. The Huber needle assembly recited in claim 1, wherein the lower body further comprises a needle barrier separating the well from the lower body needle aperture.

3. The Huber needle assembly recited in claim 1, wherein at least a portion of the well bottom surface is at least one of flat, contoured, angled, undulated, and sloped.

4. The Huber needle assembly recited in claim 1, wherein the well extends all the way around the lower body needle aperture.

5. The Huber needle assembly recited in claim 1, wherein the well is formed on a portion of the lower body that is positioned at the front of the assembly.

6. The Huber needle assembly recited in claim 1, wherein:
   the connector is connected to the upper body by an upper body connection;
   the connector is connected to the lower body by a lower body connection; and,
   at least one of a geometric plane of the upper body connection and a geometric plane of the lower body connection is offset from the axis of the operational longitudinal direction.

7. The Huber needle assembly recited in claim 1, wherein the enveloping structure is configured to envelope the needle tip after the needle tip has entered the enveloping structure, preventing exposure of the needle tip to an environment outside of the enveloping structure.

8. The Huber needle assembly recited in claim 1, wherein the enveloping structure further comprises a flange extension disposed on the top of the lower body.

9. The Huber needle assembly recited in claim 1, wherein biasing the needle comprises at least one of:
   urging the needle in a forward operational latitudinal direction when the upper body is moved away from the lower body; and,
   preventing the needle tip from moving in a rearward operational latitudinal direction after the needle tip has entered the enveloping structure.

10. The Huber needle assembly recited in claim 9, wherein the biasing of the needle further comprises generating an audible sound.

11. The Huber needle assembly recited in claim 1, wherein the advancing assist protrudes from a lower portion of the connector, whereby the movement of the upper body away from the lower body forces the advancing assist to contact the needle shaft.

12. The Huber needle assembly recited in claim 1, wherein the advancing assist comprises a channel to guide the needle shaft into a detent or recess of the advancing assist.

* * * * *